United States Patent
Burkhalter et al.

(10) Patent No.: US 10,684,265 B2
(45) Date of Patent: Jun. 16, 2020

(54) METHODS AND APPARATUSES FOR DETECTING VOLATILE ORGANIC COMPOUNDS IN GLASS PACKAGING PROCESSES

(71) Applicant: CORNING INCORPORATED, Corning, NY (US)

(72) Inventors: Robert Scott Burkhalter, Painted Post, NY (US); Andrei Gennadyevich Fadeev, Elmira, NY (US); John Stephen Peanasky, Big Flats, NY (US); David Charles Sauer, Horseheads, NY (US)

(73) Assignee: CORNING INCORPORATED, Corning, NY (US)

( * ) Notice: Subject to any disclaimer, the term of this patent is extended or adjusted under 35 U.S.C. 154(b) by 130 days.

(21) Appl. No.: 15/693,693

(22) Filed: Sep. 1, 2017

(65) Prior Publication Data
US 2018/0067091 A1    Mar. 8, 2018

Related U.S. Application Data

(60) Provisional application No. 62/382,855, filed on Sep. 2, 2016.

(51) Int. Cl.
*G01N 33/00* (2006.01)
*A61L 2/04* (2006.01)
*G01N 33/38* (2006.01)

(52) U.S. Cl.
CPC .......... *G01N 33/0016* (2013.01); *A61L 2/04* (2013.01); *G01N 33/0047* (2013.01); *G01N 33/386* (2013.01)

(58) Field of Classification Search
CPC .......... G01N 33/0016; G01N 33/0009; G01N 33/0047; A61L 2/04; C03C 17/28
(Continued)

(56) References Cited

U.S. PATENT DOCUMENTS 5,906,688 A * 5/1999 Ohmi .................. C23C 8/14
148/284
6,165,251 A * 12/2000 Lemieux ............ B01D 53/04
95/82
(Continued)

FOREIGN PATENT DOCUMENTS

KR    20040089318 A  * 10/2004
KR    20040089318 A    10/2004
(Continued)

OTHER PUBLICATIONS

Translated KR-20040089318-A (Year: 2004).*
(Continued)

*Primary Examiner* — Natalie Huls
*Assistant Examiner* — Monica S Young
(74) *Attorney, Agent, or Firm* — Dinsmore & Shohl LLP

(57) ABSTRACT

A method for measuring volatile organic compounds includes loading glass containers into an oven, heating the oven, purging the oven with dry clean air, collecting a volumetric portion of an oven exhaust, trapping volatile organic compounds from the volumetric portion, and measuring the volatile organic compounds trapped in the trap. The one or more glass containers are in-tact while measuring the VOCs of the coated glass container. An apparatus includes an oven having an interior volume that is capable of holding one or more in-tact glass containers, a flow meter fluidly connected to the first trap, and a pump fluidly connected to the flow meter. The first trap collects volatile organic compounds from a volumetric portion of the oven exhaust gas. The pump controls a flow rate of the volumetric portion of the oven exhaust gas across the first trap.

19 Claims, 4 Drawing Sheets

(58) Field of Classification Search
USPC .......................................................... 73/23.2
See application file for complete search history.

(56) References Cited

U.S. PATENT DOCUMENTS

| | | | | |
|---|---|---|---|---|
| 2005/0075461 A1* | 4/2005 | Morimoto | .................. | C08F 6/00 |
| | | | | 525/326.3 |
| 2009/0226849 A1* | 9/2009 | Tsukamoto | ............ | G03B 27/52 |
| | | | | 430/325 |
| 2010/0298738 A1* | 11/2010 | Felts | ......................... | B05D 1/62 |
| | | | | 600/576 |
| 2013/0171456 A1* | 7/2013 | Fadeev | .................. | C03C 17/005 |
| | | | | 428/429 |
| 2014/0001076 A1* | 1/2014 | Fadeev | .................. | C03C 17/005 |
| | | | | 206/524.3 |
| 2014/0034544 A1* | 2/2014 | Chang | .................... | B65D 25/14 |
| | | | | 206/524.3 |
| 2014/0151370 A1* | 6/2014 | Chang | .................... | A61J 1/065 |
| | | | | 220/62.15 |
| 2015/0098084 A1* | 4/2015 | Felts | .................... | A61M 5/3129 |
| | | | | 356/432 |
| 2015/0166217 A1* | 6/2015 | Deutschle | ............ | B65D 25/108 |
| | | | | 53/425 |
| 2016/0017170 A1* | 1/2016 | Lee | ....................... | C08F 230/02 |
| | | | | 257/40 |
| 2016/0251260 A1 | 9/2016 | Bayne et al. | | |
| 2018/0116907 A1* | 5/2018 | Fadeev | ..................... | A61J 1/00 |

FOREIGN PATENT DOCUMENTS

| | | | |
|---|---|---|---|
| KR | 20070090508 A | * | 9/2007 |
| KR | 20070090508 A | | 9/2007 |
| WO | 2011143509 A1 | | 11/2011 |

OTHER PUBLICATIONS

Translate KR-20070090508-A (Year: 2007).*
International Search Report & Written Opinion dated Dec. 5, 2017, for PCT/US2017/049930 filed Sep. 1, 2017. pp. 1-10.

* cited by examiner

METHODS AND APPARATUSES FOR DETECTING VOLATILE ORGANIC COMPOUNDS IN GLASS PACKAGING PROCESSES

CROSS REFERENCE TO RELATED APPLICATIONS

The present application claims priority to U.S. Provisional Application No. 62/382,855 filed Sep. 2, 2016, entitled, "Methods and Apparatuses for Detecting Volatile Organic Compounds in Glass Packaging Processes," the entirety of which is incorporated by reference herein.

BACKGROUND

Field

The present specification generally relates to detecting volatile organic compounds in glass packaging processes. More specifically, the present specification is directed to methods and apparatuses for detecting volatile organic compounds in pharmaceutical glass packaging processes.

Technical Background

Historically, glass has been used as the preferred material for packaging pharmaceuticals because of its hermeticity, optical clarity, and excellent chemical durability relative to other materials. Specifically, the glass used in pharmaceutical packaging must have adequate chemical durability so as to not affect the stability of the pharmaceutical compositions contained therein. Glasses having suitable chemical durability include those glass compositions within the ASTM standard E438.92 'Type IA' and 'Type IB' glass compositions which have a proven history of chemical durability. In general terms, chemically durable glasses are glasses whose constituent components do not dissolve from the glass when the glass is exposed to a solution for extended periods of time. However, even chemically durable glass compositions have a tendency to delaminate or shed glass particles following exposure to pharmaceutical solutions.

In addition, the glass compositions used for pharmaceutical packaging may be ion-exchanged to improve mechanical strength, and they may be coated on the exterior with a thermally stable lubricous coating capable of withstanding depyrogenation conditions, which preserves the mechanical strength of the glass packaging. Under the depyrogenation conditions, the coating may undergo oxidation and degradation and results in evolution of volatile organic compounds (VOCs). The amounts of VOCs evolved depend on the coating chemistry, coating thickness, coated surface area, coating deposition processing conditions, and depyrogenation temperature. The chemical composition of VOCs is also dependent on the residence time of the VOCs at the depyrogenation temperature, as VOCs are less thermally stable when compared to the coating and would undergo thermoxidative degradation at an accelerated rate. Evolution of VOCs can potentially result in presence of undesirable compounds on the interior of the container or induce a sense of perceptible smell in humans with elevated olfactory sensitivity.

Conventional methods for measuring VOCs of glass articles of any shape involve breaking the glass articles into small pieces and loading the small pieces into a column. The column is then heated and gasses are flowed through the column. The gasses that have flowed through the column are then collected in a trap that isolates and collects VOCs. The collected VOCs from the trap can then be measured using conventional component measuring techniques, such as gas chromatography and mass spectrometry. However, these conventional methods have at least three draw backs. First, the glass articles must be broken in order to measure the VOCs, which opens a possibility for sample contamination and partial loss of sample. Second, the columns have limited capacity and only a limited number of glass articles can be tested at a time. Third, the results of such tests are not necessarily accurate because crushing of the glass article also increases the surface area of the coating thus increasing coating oxidation and degradation. The typical analytical equipment and the scale at which VOCs analysis is performed is not conducive to maintaining a desirable residence time for VOCs at the temperature of depyrogenation.

Accordingly, a need exists for apparatuses and processes that identify VOCs evolving from the coated container under real depyrogenation conditions and that measures the amounts and composition of VOCs based on the depyrogenation process established for a specific size and shape of the glass container and the specific depyrogenation equipment utilized in the process.

SUMMARY

Embodiments disclosed herein describe a method for measuring volatile organic compounds evolved from coated glass containers is provided. The method includes loading one or more glass containers into an oven, heating the oven to a heat treatment temperature, purging the oven with dry clean air, collecting at least a volumetric portion of an oven exhaust, trapping volatile organic compounds from the volumetric portion of the oven exhaust in a trap, and measuring the volatile organic compounds trapped in the trap. The one or more glass containers are in-tact while measuring the VOCs of the coated glass container.

Other embodiments disclosed herein describe an apparatus for measuring an evolution of volatile organic compounds from a coated glass container. The apparatus includes an oven having an interior volume that is capable of holding one or more in-tact glass containers, a first trap fluidly connected to the oven, a flow meter fluidly connected to the first trap, and a pump fluidly connected to the flow meter. A volumetric portion of an oven exhaust gas is directed to the first trap, and the first trap collects volatile organic compounds from the volumetric portion of the oven exhaust gas. The pump controls a flow rate of the volumetric portion of the oven exhaust gas across the first trap.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
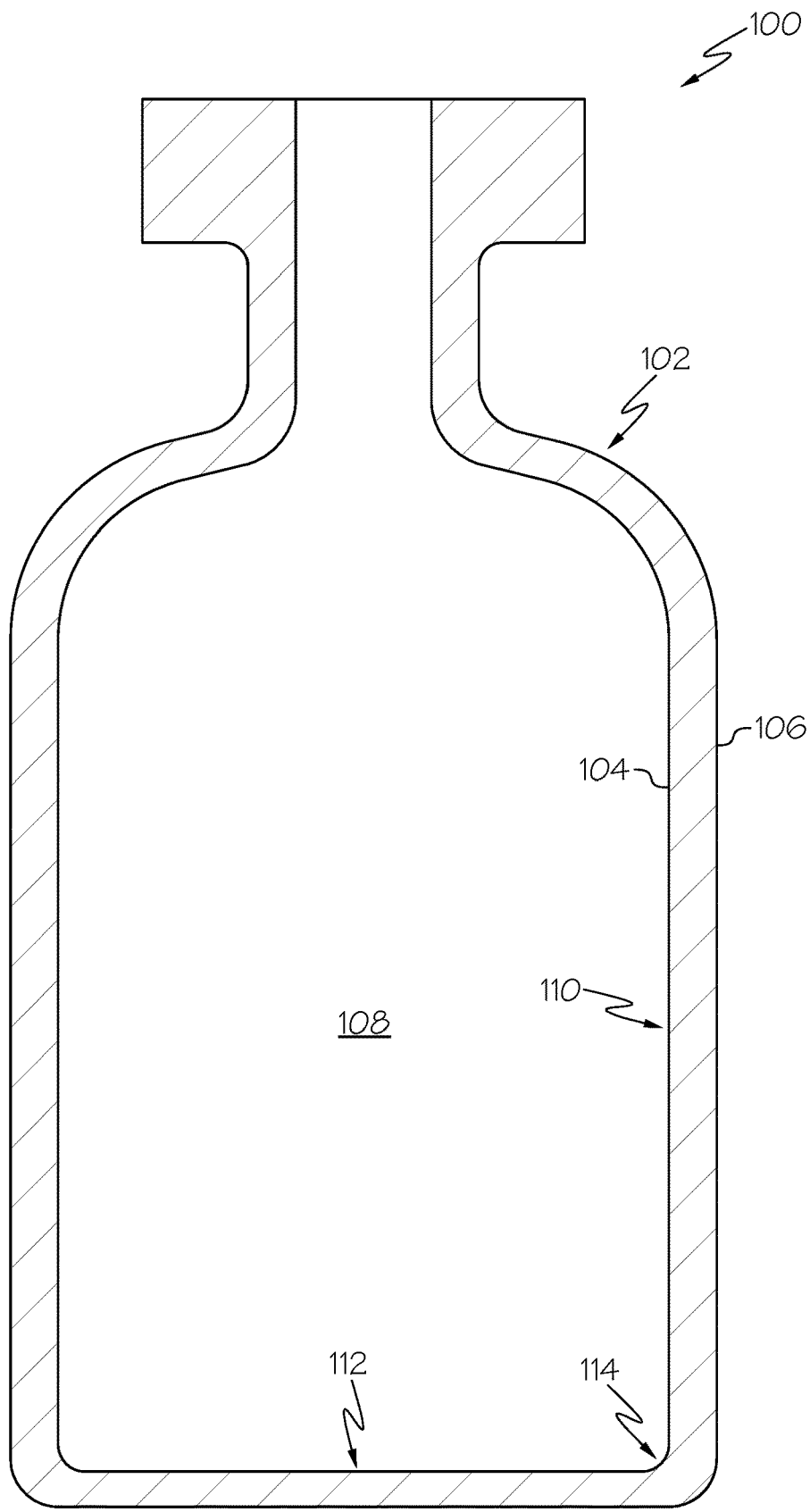
FIG. 1 schematically depicts a cross section of a glass container, specifically a glass vial, according to one or more embodiments described herein.

Reference will now be made in detail to various embodiments of apparatuses and methods for detecting VOCs in glass packaging processes, examples of which are illustrated in the accompanying drawings. Whenever possible, the same reference numerals will be used throughout the drawings to refer to the same or like parts. In one embodiment, a method for measuring volatile organic compounds emitted from one or more glass containers is discloses. The method comprises: loading the one or more glass containers into an oven; heating the oven to a heat treatment temperature; collecting at least a volumetric portion of an oven exhaust; trapping volatile organic compounds from the collected volumetric portion of the oven exhaust in a trap; and measuring the volatile organic compounds trapped in the trap. The one or more glass containers are in-tact. Another embodiment discloses an apparatus for measuring the evolution of volatile organic compounds from a glass container. The apparatus comprises: an oven having an interior volume that is capable of holding one or more in-tact glass containers; a first trap fluidly connected to the oven; a flow meter fluidly connected to the first trap; and a pump fluidly connected to the flow meter. The apparatus directs a volumetric portion of an oven exhaust gas to the first trap, the first trap collects volatile organic compounds from the volumetric portion of the oven exhaust gas, and the pump controls a flow rate of the volumetric portion of the oven exhaust gas across the first trap.

The term "chemical durability," as used herein, refers to the ability of the glass composition to resist degradation upon exposure to specified chemical conditions. Specifically, the chemical durability of the glass compositions described herein was assessed according to 3 established material testing standards: DIN 12116 dated March 2001 and entitled "Testing of glass—Resistance to attack by a boiling aqueous solution of hydrochloric acid—Method of test and classification"; ISO 695:1991 entitled "Glass—Resistance to attack by a boiling aqueous solution of mixed alkali—Method of test and classification"; ISO 720:1985 entitled "Glass—Hydrolytic resistance of glass grains at 121 degrees C.—Method of test and classification"; and ISO 719:1985 "Glass—Hydrolytic resistance of glass grains at 98 degrees C.—Method of test and classification." Each standard and the classifications within each standard are described in further detail herein. Alternatively, the chemical durability of a glass composition may be assessed according to USP <660> entitled "Surface Glass Test," and/or European Pharmacopeia 3.2.1 entitled "Glass Containers For Pharmaceutical Use" which assess the durability of the surface of the glass.

The methods and apparatuses described herein may be used to measure the VOCs emitted from any glass container that has a coating and the coating contains organic compounds. The type of coating is not particularly limited. However, in embodiments, the coating may be a low-friction coating, as described below.

Glass containers may be subject to damage, such as impact damage, scratches and/or abrasions, as the containers are processed and filled. Such damage is often caused by contact between individual glass containers or contact between the glass containers and manufacturing equipment. This damage generally decreases the mechanical strength of the container and may lead to through-cracks which can compromise the integrity of the contents of the container. Accordingly, in some embodiments described herein, the glass containers further include a low-friction coating positioned around at least a portion of the outer surface of the body. In some embodiments, the low-friction coating may be positioned on at least the outer surface of the body of the glass container while, in other embodiments, one or more intermediate coatings may be positioned between the low-friction coating and the outer surface of the body, such as when an inorganic coating is utilized to compressively stress the surface of the body. The low-friction coating decreases the coefficient of friction of the portion of the body with the coating and, as such, decreases the occurrence of abrasions and surface damage on the outer surface of the glass body. In essence, the coating allows the container to "slip" relative to another object (or container) thereby reducing the possibility of surface damage on the glass. Moreover, the low-friction coating also cushions the body of the glass container, thereby lessening the effect of blunt impact damage to the glass container. Exemplary coatings are disclosed in U.S. patent application Ser. No. 14/075,630 filed on Nov. 8, 2013, which is incorporated herein by reference in its entirety.

A lower or reduced coefficient of friction may impart improved strength and durability to the glass article by mitigating frictive damage to the glass. Further, the low-friction coating may maintain the aforementioned improved strength and durability characteristics following exposure to elevated temperatures and other conditions, such as those experienced during packaging and pre-packaging steps utilized in packaging pharmaceuticals, such as, for example, depyrogenation, autoclaving and the like. Accordingly, the low-friction coatings and glass articles with the low-friction coating are thermally stable.

The low-friction coating may generally comprise a coupling agent, such as a silane, and a polymer chemical composition, such as a polyimide. In some embodiments, the coupling agent may be disposed in a coupling agent layer positioned on the surface of the glass article and the polymer chemical composition may be disposed in a polymer layer positioned on the coupling agent layer. In other embodiments, the coupling agent and the polymer chemical composition may be mixed in a single layer. Suitable coatings are described in U.S. patent application Ser. No. 13/780,740 filed on Feb. 28, 2013.

Referring to the embodiments described above, the silane chemical composition may be aromatic chemical compositions. As used herein, an aromatic chemical composition contains one or more six-carbon rings characteristic of the benzene series and related organic moieties. The aromatic silane chemical composition may be an alkoxysilane such as, but not limited to, a dialkoxysilane chemical composition, hydrolysate thereof, or oligomer thereof, or a trialkoxysilane chemical composition, hydrolysate thereof, or oligomer thereof. In some embodiments, the aromatic silane may comprise an amine moiety, and may be an alkoxysilane comprising an amine moiety. In another embodiment, the aromatic silane chemical composition may be an aromatic alkoxysilane chemical composition, an aromatic acyloxysilane chemical composition, an aromatic halogen silane chemical composition, or an aromatic aminosilane chemical composition. In another embodiment, the aromatic silane chemical composition may be selected from the group consisting of aminophenyl, 3-(m-aminophenoxy) propyl, N-phenylaminopropyl, or (chloromethyl) phenyl substituted alkoxy, acyloxy, halogen, or amino silanes. For example, the aromatic alkoxysilane may be, but is not limited to, aminophenyltrimethoxy silane (sometimes referred to herein as "APhTMS"), aminophenyldimethoxy silane, aminophenyltriethoxy silane, aminophenyldiethoxy silane, 3-(m-aminophenoxy) propyltrimethoxy silane, 3-(m-aminophenoxy) propyldimethoxy silane, 3-(m-aminophenoxy) propyltriethoxy silane, 3-(m-aminophenoxy) propyldiethoxy silane, N-phenylaminopropyltrimethoxysilane, N-phenylaminopropyldimethoxysilane, N-phenylaminopropyltriethoxysilane, N-phenylaminopropyldiethoxysilane, hydrolysates thereof, or oligomerized chemical composition thereof. In an exemplary embodiment, the aromatic silane chemical composition may be aminophenyltrimethoxy silane.

Referring again to the embodiments described above, the silane chemical composition may be aliphatic chemical compositions. As used herein, an aliphatic chemical composition is non-aromatic, such as a chemical composition having an open chain structure, such as, but not limited to, alkanes, alkenes, and alkynes. For example, in some embodiments, the coupling agent may comprise a chemical composition that is an alkoxysilane and may be an aliphatic alkoxysilane such as, but not limited to, a dialkoxysilane chemical composition, a hydrolysate thereof, or an oligomer thereof, or a trialkoxysilane chemical composition, a hydrolysate thereof, or an oligomer thereof. In some embodiments, the aliphatic silane may comprise an amine moiety, and may be an alkoxysilane comprising an amine moiety, such as an aminoalkyltrialkoxysilane. In one embodiment, an aliphatic silane chemical composition may be selected from the group consisting of 3-aminopropyl, N-(2-aminoethyl)-3-aminopropyl, vinyl, methyl, N-phenylaminopropyl, (N-phenylamino)methyl, N-(2-Vinylbenzylaminoethyl)-3-aminopropyl substituted alkoxy, acyloxy, halogen, or amino silanes, hydrolysates thereof, or oligomers thereof. Aminoalkyltrialkoxysilanes, include, but are not limited to, 3-aminopropyltrimethoxy silane (sometimes referred to herein as "GAPS"), 3-aminopropyldimethoxy silane, 3-aminopropyltriethoxy silane, 3-aminopropyldiethoxy silane, N-(2-aminoethyl)-3-aminopropyltrimethoxysilane, N-(2-aminoethyl)-3-aminopropyldimethoxysilane, N-(2-aminoethyl)-3-aminopropyltriethoxysilane, N-(2-aminoethyl)-3-aminopropyldiethoxysilane, hydrolysates thereof, and oligomerized chemical composition thereof. In other embodiments, the aliphatic alkoxysilane chemical composition may not contain an amine moiety, such as an alkyltrialkoxysilane or alkylbialkoxysilane. Such alkyltrialkoxysilanes or alkylbialkoxysilanes include, but are not limited to, vinyltrimethoxy silane, vinyldimethoxy silane, vinyltriethoxy silane, vinyldiethoxy silane, methyltrimethoxysilane, methyldimethoxysilane, methyltriethoxysilane, methyldiethoxysilane, hydrolysates thereof, or oligomerized chemical composition thereof. In an exemplary embodiment, the aliphatic silane chemical composition is 3-aminopropyltrimethoxy silane.

As noted herein, the low-friction coating also includes a polymer chemical composition. The polymer chemical composition may be a thermally stable polymer or mixture of polymers, such as but not limited to, polyimides, polybenzimidazoles, polysulfones, polyetheretherketones, polyetherimides, polyamides, polyphenyls, polybenzothiazoles, polybenzoxazoles, polybisthiazoles, and polyaromatic heterocyclic polymers with and without organic or inorganic fillers. The polymer chemical composition may be formed from other thermally stable polymers, such as polymers that do not degrade at temperatures in the range of from 200° C. to 400° C., including 250° C., 300° C., and 350° C. These polymers may be applied with or without a coupling agent.

In one embodiment, the polymer chemical composition is a polyimide chemical composition. If the low-friction coating comprises a polyimide, the polyimide composition may be derived from a polyamic acid, which is formed in a solution by the polymerization of monomers. One such polyamic acid is Novastrat® 800 (commercially available from NeXolve). A curing step imidizes the polyamic acid to form the polyimide. The polyamic acid may be formed from the reaction of a diamine monomer, such as a diamine, and an anhydride monomer, such as a dianhydride. As used herein, polyimide monomers are described as diamine monomers and dianhydride monomers. However, it should be understood that while a diamine monomer comprises two amine moieties, in the description that follows, any monomer comprising at least two amine moieties may be suitable as a diamine monomer. Similarly, it should be understood that while a dianhydride monomer comprises two anhydride moieties, in the description that follows any monomer comprising at least two anhydride moieties may be suitable as a dianhydride monomer. The reaction between the anhydride moieties of the anhydride monomer and amine moieties of the diamine monomer forms the polyamic acid. Therefore, as used herein, a polyimide chemical composition that is formed from the polymerization of specified monomers refers to the polyimide that is formed following the imidization of a polyamic acid that is formed from those specified monomers. Generally, the molar ratio of the total anhydride monomers and diamine monomers may be about 1:1. While the polyimide may be formed from only two distinct chemical compositions (one anhydride monomer and one diamine monomer), at least one anhydride monomer may be polymerized and at least one diamine monomer may be polymerized to from the polyimide. For example, one anhydride monomer may be polymerized with two different diamine monomers. Any number of monomer specie combinations may be used. Furthermore, the ratio of one anhydride monomer to a different anhydride monomer, or one or more diamine monomer to a different diamine monomer may be any ratio, such as between 1:0.1 to 0.1:1, such as about 1:9, 1:4, 3:7, 2:3, 1:1, 3:2, 7:3, 4:1 or 1:9.

The anhydride monomer from which, along with the diamine monomer, the polyimide is formed may comprise any anhydride monomer. In one embodiment, the anhydride monomer comprises a benzophenone structure. In an exemplary embodiment, benzophenone-3,3',4,4'-tetracarboxylic dianhydride may be at least one of the anhydride monomer from which the polyimide is formed. In other embodiments, the diamine monomer may have an anthracene structure, a phenanthrene structure, a pyrene structure, or a pentacene structure, including substituted versions of the above mentioned dianhydrides.

The diamine monomer from which, along with the anhydride monomer, the polyimide is formed may comprise any diamine monomer. In one embodiment, the diamine monomer comprises at least one aromatic ring moiety. The diamine monomer may have one or more carbon molecules connecting two aromatic ring moieties together. Alternatively, the diamine monomer may have two aromatic ring moieties that are directly connected and not separated by at least one carbon molecule.

Two different chemical compositions of diamine monomers may form the polyimide. In one embodiment, a first diamine monomer comprises two aromatic ring moieties that are directly connected and not separated by a linking carbon molecule, and a second diamine monomer comprises two aromatic ring moieties that are connected with at least one carbon molecule connecting the two aromatic ring moieties. In one exemplary embodiment, the first diamine monomer, the second diamine monomer, and the anhydride monomer have a molar ratio (first diamine monomer:second diamine monomer:anhydride monomer) of about 0.465:0.035:0.5. However, the ratio of the first diamine monomer and the second diamine monomer may vary in a range of 0.01:0.49 to 0.40:0.10, while the anhydride monomer ratio remains at about 0.5.

In one embodiment, the polyimide composition is formed from the polymerization of at least a first diamine monomer, a second diamine monomer, and an anhydride monomer, wherein the first and second diamine monomers are different chemical compositions. In one embodiment, the anhydride monomer is a benzophenone, the first diamine monomer comprises two aromatic rings directly bonded together, and the second diamine monomer comprises two aromatic rings bonded together with at least one carbon molecule connecting the first and second aromatic rings. The first diamine monomer, the second diamine monomer, and the anhydride monomer may have a molar ratio (first diamine monomer: second diamine monomer:anhydride monomer) of about 0.465:0.035:0.5.

In an exemplary embodiment, the first diamine monomer is ortho-Tolidine, the second diamine monomer is 4,4'-methylene-bis(2-methylaniline), and the anhydride monomer is benzophenone-3,3',4,4'-tetracarboxylic dianhydride. The first diamine monomer, the second diamine monomer, and the anhydride monomer may have a molar ratio (first diamine monomer:second diamine monomer:anhydride monomer) of about 0.465:0.035:0.5.

In some embodiments, the polyimide may be formed from the polymerization of one or more of: bicyclo[2.2.1]heptane-2,3,5,6-tetracarboxylic dianhydride, cyclopentane-1,2,3,4-tetracarboxylic 1,2;3,4-dianhydride, bicyclo[2.2.2]octane-2,3,5,6-tetracarboxylic dianhydride, 4arH,8acH)-decahydro-1t,4t:5c,8c-dimethanonaphthalene-2t,3t,6c,7c-tetracarboxylic 2,3:6,7-dianhydride, 2c,3c,6c,7c-tetracarboxylic 2,3:6,7-dianhydride, 5-endo-carboxymethylbicyclo[2.2.1]-heptane-2-exo,3-exo,5-exo-tricarboxylic acid 2,3:5,5-dianhydride, 5-(2,5-Dioxotetrahydro-3-furanyl)-3-methyl-3-cyclohexene-1,2-dicarboxylic anhydride, isomers of Bis(aminomethyl)bicyclo[2.2.1]heptane, or 4,4'-Methylenebis(2-methylcyclohexylamine), Pyromellitic dianhydride (PMDA) 3,3',4,4'-Biphenyl dianhydride (4,4'-BPDA), 3,3', 4,4'-Benzophenone dianhydride (4,4'-BTDA), 3,3',4,4'-Oxydiphthalic anhydride (4,4'-ODPA), 1,4-Bis(3,4-dicarboxyl-phenoxy)benzene dianhydride (4,4'-HQDPA), 1,3-Bis(2,3-dicarboxyl-phenoxy)benzene dianhydride (3,3'-HQDPA), 4,4'-Bis(3,4-dicarboxyl phenoxyphenyl)-isopropylidene dianhydride (4,4'-BPADA), 4,4'-(2,2,2-Trifluoro-1-pentafluorophenylethylidene) diphthalic dianhydride (3FDA), 4,4'-Oxydianiline (ODA), m-Phenylenediamine (MPD), p-Phenylenediamine (PPD), m-Toluenediamine (TDA), 1,4-Bis(4-aminophenoxy)benzene (1,4,4-APB), 3,3'-(m-Phenylenebis(oxy))dianiline (APB), 4,4'-Diamino-3,3'-dimethyldiphenylmethane (DMMDA), 2,2'-Bis(4-(4-aminophenoxy)phenyl)propane (BAPP), 1,4-Cyclohexanediamine 2,2'-Bis[4-(4-amino-phenoxy) phenyl] hexafluoroisopropylidene (4-BDAF), 6-Amino-1-(4'-aminophenyl)-1,3,3-trimethylindane (DAPI), Maleic anhydride (MA), Citraconic anhydride (CA), Nadic anhydride (NA), 4-(Phenylethynyl)-1,2-benzenedicarboxylic acid anhydride (PEPA), 4,4'-diaminobenzanilide (DABA), 4,4'-(hexafluoroisopropylidene)di-phthalicanhydride (6-FDA), Pyromellitic dianhydride, benzophenone-3,3',4,4'-tetracarboxylic dianhydride, 3,3',4,4'-biphenyltetracarboxylic dianhydride, 4,4'-(hexafluoroisopropylidene)diphthalic anhydride, perylene-3,4,9,10-tetracarboxylic dianhydride, 4,4'-oxydiphthalic anhydride, 4,4'-(hexafluoroisopropylidene)diphthalic anhydride, 4,4'-(4,4'-Isopropylidenediphenoxy)bis (phthalic anhydride), 1,4,5,8-Naphthalenetetracarboxylic dianhydride, 2,3,6,7-Naphthalenetetracarboxylic dianhydride, as well as those materials described in U.S. Pat. Nos. 7,619,042, 8,053,492, 4,880,895, 6,232,428, 4,595,548, WO Pub. No. 2007/016516, U.S. Pat. Pub. No. 2008/0214777, U.S. Pat. Nos. 6,444,783, 6,277,950, and 4,680,373, which are incorporated herein by reference in their entirety. In another embodiment, the polyamic acid solution from which the polyimide is formed may comprise poly (pyromellitic dianhydride-co-4,4'-oxydianiline) amic acid (commercially available from Aldrich).

As referenced above, the coating may have a low coefficient of friction. The coefficient of friction ($\mu$) of the portion of the coated glass container with the low-friction coating may have a lower coefficient of friction than a surface of an uncoated glass container formed from a same glass composition. A coefficient of friction ($\mu$) is a quantitative measurement of the friction between two surfaces and is a function of the mechanical and chemical properties of the first and second surfaces, including surface roughness, as well as environmental conditions such as, but not limited to, temperature and humidity. As used herein, a coefficient of friction measurement for a coated glass container is reported as the coefficient of friction between the outer surface of a first glass container and the outer surface of second glass container which is identical to the first glass container, wherein the first and second glass containers have the same body and the same coating composition (when applied) and have been exposed to the same environments prior to fabrication, during fabrication, and after fabrication. Unless otherwise denoted herein, the coefficient of friction refers to the maximum coefficient of friction measured with a normal load of 30 N measured on a vial-on-vial testing jig. However, it should be understood that a coated glass container which exhibits a maximum coefficient of friction at a specific applied load will also exhibit the same or better (i.e., lower) maximum coefficient of friction at a lesser load. For example, if a coated glass container exhibits a maximum coefficient of friction of 0.5 or lower under an applied load of 50 N, the coated glass container will also exhibit a maximum coefficient of friction of 0.5 or lower under an applied load of 25 N.

In the embodiments described herein, the coefficient of friction of the glass containers (both coated and uncoated) is measured with a vial-on-vial testing jig. This measurement technique and corresponding device are described in U.S.

patent application Ser. No. 13/780,740 filed on Feb. 28, 2013, which is incorporated herein by reference in its entirety.

In the embodiments described herein, the portion of the coated glass container with the low-friction coating has a coefficient of friction of less than or equal to 0.7 relative to a like-coated glass container, as determined with the vial-on-vial testing jig. In other embodiments, the coefficient of friction may be less than or equal to 0.6, or even less than or equal to 0.5. In some embodiments, the portion of the coated glass container with the low-friction coating has a coefficient of friction of less than or equal to 0.4, or even less than or equal to 0.3. Coated glass containers with coefficients of friction less than or equal to 0.7 generally exhibit improved resistance to frictive damage and, as a result, have improved mechanical properties. For example, conventional glass containers (without a low-friction coating) may have a coefficient of friction of greater than 0.7.

In some embodiments described herein, the coefficient of friction of the portion of the coated glass container with the low-friction coating is at least 20% less than a coefficient of friction of a surface of an uncoated glass container formed from a same glass composition. For example, the coefficient of friction of the portion of the coated glass container with the low-friction coating may be at least 20% less, at least 25% less, at least 30% less, at least 40% less, or even at least 50% less than a coefficient of friction of a surface of an uncoated glass container formed from a same glass composition.

In some embodiments, the portion of the coated glass container with the low-friction coating may have a coefficient of friction of less than or equal to 0.7 after exposure to a temperature of about 260° C., about 270° C., about 280° C., about 290° C., about 300° C., about 310° C., about 320° C., about 330° C., about 340° C., about 350° C., about 360° C., about 370° C., about 380° C., about 390° C., or about 400° C., for a period of time of 30 minutes. In other embodiments, the portion of the coated glass container with the low-friction coating may have a coefficient of friction of less than or equal to 0.7, (i.e., less than or equal to 0.6, less than or equal to 0.5, less than or equal to 0.4, or even less than or equal to 0.3) after exposure to a temperature of about 260° C., about 270° C., about 280° C., about 290° C., about 300° C., about 310° C., about 320° C., about 330° C., about 340° C., about 350° C., about 360° C., about 370° C., about 380° C., about 390° C., or about 400° C., for a period of time of 30 minutes. In some embodiments, the coefficient of friction of the portion of the coated glass container with the low-friction coating may not increase by more than about 30% after exposure to a temperature of about 260° C. for 30 minutes. In other embodiments, the coefficient of friction of the portion of the coated glass container with the low-friction coating may not increase by more than about 30% (i.e., about 25%, about 20%, about 15%, or event about 10%) after exposure to a temperature of about 260° C., about 270° C., about 280° C., about 290° C., about 300° C., about 310° C., about 320° C., about 330° C., about 340° C., about 350° C., about 360° C., about 370° C., about 380° C., about 390° C., or about 400° C., for a period of time of 30 minutes. In other embodiments, the coefficient of friction of the portion of the coated glass container with the low-friction coating may not increase by more than about 0.5 (i.e., about 0.45, about 0.04, about 0.35, about 0.3, about 0.25, about 0.2, about 0.15, about 0.1, or event about 0.5) after exposure to a temperature of about 260° C., about 270° C., about 280° C., about 290° C., about 300° C., about 310° C., about 320° C., about 330° C., about 340° C., about 350° C., about 360° C., about 370° C., about 380° C., about 390° C., or about 400° C., for a period of time of 30 minutes. In some embodiments, the coefficient of friction of the portion of the coated glass container with the low-friction coating may not increase at all after exposure to a temperature of about 260° C., about 270° C., about 280° C., about 290° C., about 300° C., about 310° C., about 320° C., about 330° C., about 340° C., about 350° C., about 360° C., about 370° C., about 380° C., about 390° C., or about 400° C., for a period of time of 30 minutes.

In some embodiments, the portion of the coated glass container with the low-friction coating may have a coefficient of friction of less than or equal to 0.7 after being submerged in a water bath at a temperature of about 70° C. for 10 minutes. In other embodiments, the portion of the coated glass container with the low-friction coating may have a coefficient of friction of less than or equal to 0.7, (i.e., less than or equal to 0.6, less than or equal to 0.5, less than or equal to 0.4, or even less than or equal to 0.3) after being submerged in a water bath at a temperature of about 70° C. for 5 minutes, 10 minutes, 20 minutes, 30 minutes, 40 minutes, 50 minutes, or even 1 hour. In some embodiments, the coefficient of friction of the portion of the coated glass container with the low-friction coating may not increase by more than 30% after being submerged in a water bath at a temperature of about 70° C. for 10 minutes. In other embodiments, the coefficient of friction of the portion of the coated glass container with the low-friction coating may not increase by more than 30% (i.e., about 25%, about 20%, about 15%, or event about 10%) after being submerged in a water bath at a temperature of about 70° C. for 5 minutes, 10 minutes, 20 minutes, 30 minutes, 40 minutes, 50 minutes, or even 1 hour. In some embodiments, the coefficient of friction of the portion of the coated glass container with the low-friction coating may not increase at all after being submerged in a water bath at a temperature of about 70° C. for 5 minutes, 10 minutes, 20 minutes, 30 minutes, 40 minutes, 50 minutes, or even 1 hour.

In some embodiments, the portion of the coated glass container with the low-friction coating may have a coefficient of friction of less than or equal to 0.7 after exposure to lyophilization conditions. In other embodiments, the portion of the coated glass container with the low-friction coating may have a coefficient of friction of less than or equal to 0.7, (i.e., less than or equal to 0.6, less than or equal to 0.5, less than or equal to 0.4, or even less than or equal to 0.3) after exposure to lyophilization conditions. In some embodiments, the coefficient of friction of the portion of the coated glass container with the low-friction coating may not increase by more than 30% after exposure to lyophilization conditions. In other embodiments, the coefficient of friction of the portion of the coated glass container with the low-friction coating may not increase by more than 30% (i.e., about 25%, about 20%, about 15%, or event about 10%) after exposure to lyophilization conditions. In some embodiments, the coefficient of friction of the portion of the coated glass container with the low-friction coating may not increase at all after exposure to lyophilization conditions.

In some embodiments, the portion of the coated glass container with the low-friction coating may have a coefficient of friction of less than or equal to 0.7 after exposure to autoclave conditions. In other embodiments, the portion of the coated glass container with the low-friction coating may have a coefficient of friction of less than or equal to 0.7, (i.e., less than or equal to 0.6, less than or equal to 0.5, less than or equal to 0.4, or even less than or equal to 0.3) after exposure to autoclave conditions. In some embodiments, the coefficient of friction of the portion of the coated glass container with the low-friction coating may not increase by more than 30% after exposure to autoclave conditions. In other embodiments, the coefficient of friction of the portion of the coated glass container with the low-friction coating may not increase by more than 30% (i.e., about 25%, about 20%, about 15%, or event about 10%) after exposure to autoclave conditions. In some embodiments, the coefficient of friction of the portion of the coated glass container with the low-friction coating may not increase at all after exposure to autoclave conditions.

The coated glass containers described herein have a horizontal compression strength. The horizontal compression strength is measured as discussed in U.S. patent application Ser. No. 13/780,740 filed on Feb. 28, 2013, which is incorporated herein by reference in its entirety. A measurement of the horizontal compression strength can be given as a failure probability at a selected normal compression load. As used herein, failure occurs when the glass container ruptures under a horizontal compression in least 50% of samples. In some embodiments, a coated glass container may have a horizontal compression strength at least 10%, 20%, or 30% greater than an uncoated vial.

The horizontal compression strength measurement may also be performed on an abraded glass container. Specifically, operation of a testing jig may create damage on the coated glass container outer surface, such as a surface scratch or abrasion that weakens the strength of the coated glass container. The glass container is then subjected to a horizontal compression procedure, wherein the container is placed between two platens with the scratch pointing outward parallel to the platens. The scratch can be characterized by the selected normal pressure applied by a vial-on-vial jig and the scratch length. Unless identified otherwise, scratches for abraded glass containers for the horizontal compression procedure are characterized by a scratch length of 20 mm created by a normal load of 30 N.

The coated glass containers can be evaluated for horizontal compression strength following a heat treatment. The heat treatment may be exposure to a temperature of about 260° C., about 270° C., about 280° C., about 290° C., about 300° C., about 310° C., about 320° C., about 330° C., about 340° C., about 350° C., about 360° C., about 370° C., about 380° C., about 390° C., or about 400° C., for a period of time of 30 minutes. In some embodiments, the horizontal compression strength of the coated glass container is not reduced by more than about 20%, 30%, or even 40% after being exposed to a heat treatment, such as those described above, and then being abraded. In one embodiment, the horizontal compression strength of the coated glass container is not reduced by more than 20% after being exposed to a heat treatment of about 260° C., about 270° C., about 280° C., about 290° C., about 300° C., about 310° C., about 320° C., about 330° C., about 340° C., about 350° C., about 360° C., about 370° C., about 380° C., about 390° C., or about 400° C., for a period of time of 30 minutes, and then being abraded.

The coated glass articles described herein may be thermally stable after heating to a temperature of at least 260° C. for a time period of 30 minutes. The phrase "thermally stable," as used herein, means that the low friction coating applied to the glass article remains substantially intact on the surface of the glass article after exposure to the elevated temperatures such that, after exposure, the mechanical properties of the coated glass article, specifically the coefficient of friction and the horizontal compression strength, are only minimally affected, if at all. This indicates that the low friction coating remains adhered to the surface of the glass following elevated temperature exposure and continues to protect the glass article from mechanical insults such as abrasions, impacts and the like.

In embodiments, the coated glass containers may be thermally stable. As described herein, the coated glass containers are considered to be thermally stable if the coefficient of friction standard and the horizontal compression strength standard are met after exposing the coated glass containers to a temperature of at least about 260° C. for a time period of about 30 minutes (i.e., the coated glass containers are thermally stable at a temperature of at least about 260° C. for a time period of about 30 minutes). The thermal stability may also be assessed at temperatures from 260° C. up to 400° C. For example, in some embodiments, the coated glass containers will be considered to be thermally stable if the standards are met at a temperature of at least 270° C., or even about 280° C. for a time period of about 30 minutes. In still other embodiments, the coated glass containers will be considered to be thermally stable if the standards are met at a temperature of at least 290° C., or even about 300° C. for a time period of about 30 minutes. In further embodiments, the coated glass containers will be considered to be thermally stable if the standards are met at a temperature of at least 310° C. or even about 320° C. for a time period of about 30 minutes. In still other embodiments, the coated glass containers will be considered to be thermally stable if the standards are met at a temperature of at least 330° C., or even about 340° C. for a time period of about 30 minutes. In yet other embodiments, the coated glass containers will be considered to be thermally stable if the standards are met at a temperature of at least 350° C., or even about 360° C. for a time period of about 30 minutes. In some other embodiments, the coated glass containers will be considered to be thermally stable if the standards are met at a temperature of at least 370° C., or even about 380° C. for a time period of 30 minutes. In still other embodiments, the coated glass containers will be considered to be thermally stable if the standards are met at a temperature of at least 390° C., or even about 400° C. for a time period of 30 minutes.

The coated glass containers disclosed herein may also be thermally stable over a range of temperatures, meaning that the coated glass containers are thermally stable by meeting the coefficient of friction standard and horizontal compression strength standard at each temperature in the range. For example, in the embodiments described herein, the coated glass containers may be thermally stable from at least 260° C. to a temperature of less than or equal to 400° C. In some embodiments, the coated glass containers may be thermally stable in a range from at least 260° C. to 350° C. In some other embodiments, the coated glass containers may be thermally stable from at least 280° C. to a temperature of less than or equal to 350° C. In still other embodiments, the coated glass containers may be thermally stable from at least 290° C. to 340° C. In another embodiment, the coated glass container may be thermally stable at a range of temperatures of 300° C. to 380° C. In another embodiment, the coated glass container may be thermally stable at a range of temperatures from 320° C. to 360° C.

Thermally stabile coated glass containers allow for at temperatures above 260° C., such as from 320° C. to 335° C., or even 360° C. to 375° C. These elevated temperatures destroy any potential DNA or unwanted organic compounds within the glass container, and sterilize the glass container. However, at these high temperatures the organic compounds, such as those in the lubricous coating, undergo oxidative degradation at least to some degree resulting in the evolution of VOCs. The amount and type of VOCs that evolve during heat treatments, such as depyrogenation, depend on the coating chemistry, the coating deposition process and conditions, and the temperature and duration of the heat treatment. The evolution of VOCs during depyrogenation, or any other heat treatment, can result in safety issues in the manufacturing facility by exposing workers to the VOCs, or can cause safety issues for either the container or the pharmaceutical.

In view of the evolution of VOCs from the coated glass containers during heat treatment, such as depyrogenation, methods and apparatuses for quickly and accurately measuring the evolution of VOCs during heat treatments, such as depyrogenation, are provided.

Figure 3:
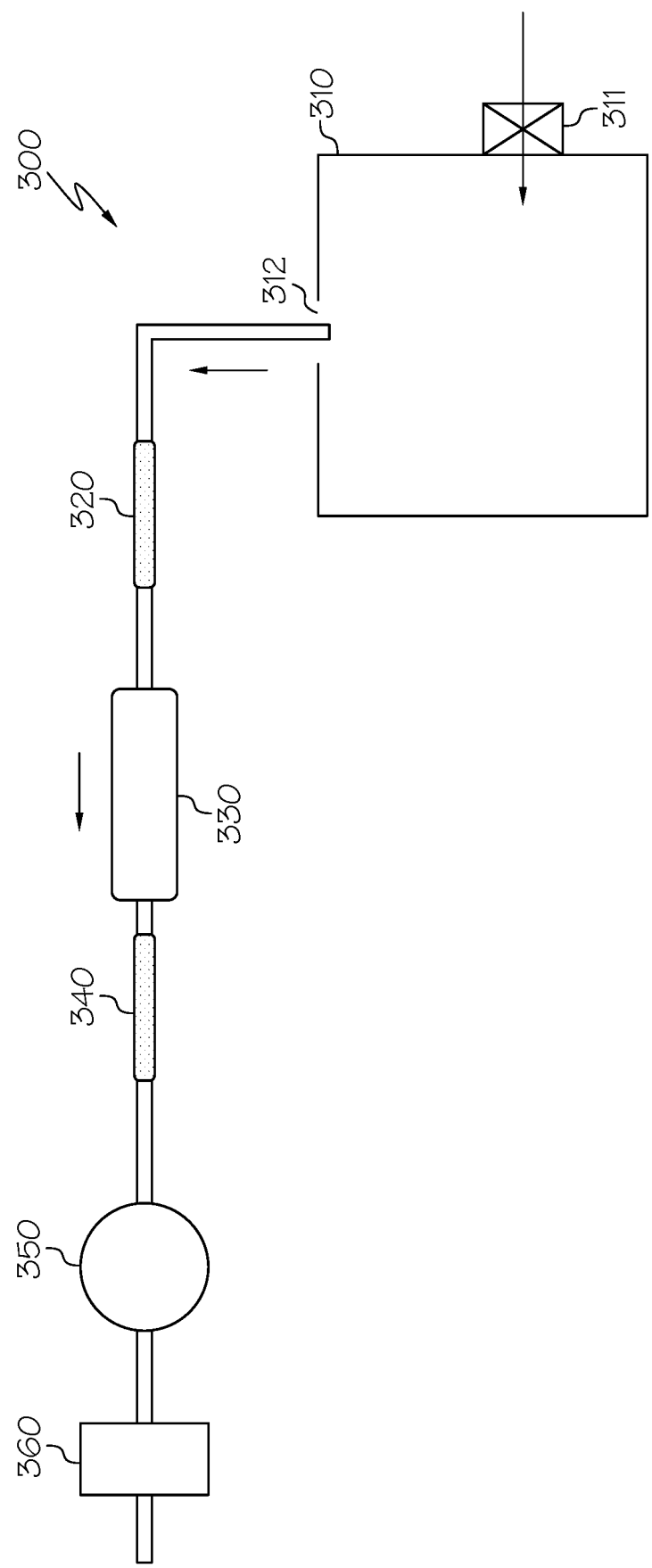
FIG. 3 schematically depicts a VOC measurement apparatus according to one or more embodiments described herein.

Referring now to FIG. 3, embodiments of a VOC measuring system 300 are described. The VOC measurement system 300 comprises an oven 310, a first trap 320, a flow meter 330, a second trap 340, a pump 350, and a flow regulator 360 that are all fluidly connected so that a gaseous exhaust stream that exits the oven 310 flows through the first trap 320, the flow meter 330, the second trap 340, the pump 350, and the flow regulator 360. It should be understood that the relative size and positioning of the components depicted in FIG. 3 are exemplary only and that other configurations of the apparatus for measuring VOCs are envisioned. Each of the components depicted in FIG. 3 will now be described in turn.

In embodiments, the oven 310 is a high-temperature oven that is capable of heating its interior to temperatures that coincide with a heat treatment temperature, such as the temperature of a depyrogenation process. In embodiments, the oven 310 is capable of heating the atmosphere of its interior to an average temperature above 260° C., such as above 320° C., or even above 360° C. In some embodiments, the oven 310 is capable of heating the atmosphere of its interior to an average temperature from greater than or equal to 320° C. to less than or equal to 335° C. In other embodiments, the oven 310 is capable of heating the atmosphere of its interior to an average temperature from greater than or equal to 360° C. to less than or equal to 375° C. In embodiments, the average temperature of the oven's interior atmosphere is measured by a temperature probe extended from a wall or the top of the oven to the geometrical center of the oven's interior volume.

In embodiments, the interior of the oven 310 is stainless steel and has a volume that can accommodate numerous in-tact glass containers. As used herein, "in-tact glass containers" refers to glass containers that have not been broken and are of a geometry and volume that is the same as an end-use glass container. In some embodiments, the interior volume of the oven 310 is at least 50 L, such as at least 55 L. In some embodiments, the interior volume of the oven is at least 60 L, such as at least 65 L. In embodiments, the interior of the oven 310 can accommodate at least 200 in-tact glass containers, such as at least 250 in-tact glass containers. In some embodiments, the interior of the oven can accommodate at least 300 in-tact glass containers, such as at least 350 in-tact glass containers. In embodiments, the oven 310 comprises a fan that circulates gases present in the interior of the oven 310 to promote uniform heating of the interior of the oven 310. An exemplary, and non-limiting, oven that may be used embodiments is an LHT 4/60 high-temperature oven manufactured by Carbolite. However, it should be understood that similar ovens may be used in embodiments.

In embodiments, the oven 310 comprises an inlet 311 that is fluidly connected to an inlet gas supply (not shown). In some embodiments, the inlet gas supply is ambient air and the inlet 311 is a vent that permits the ambient air to flow into the interior of the oven 310. In some embodiments, the inlet gas supply is treated, to produce clean dry air, which is air that is essentially free of water vapor and organics (oils, hydrocarbons, acids, bases, organics). These compounds could accumulate in the trap in excessive quantities and interfere with GC-MS analysis, or then can undergo thermoxidation in the oven environment and contribute to overall VOCs level. Where the inlet gas supply is clean dry air, the inlet 311 may be fluidly connected to the inlet gas supply by an inlet gas supply line (not shown). In embodiments, at the gas supply the clean dry air is prepared by treating ambient air through a set of filters and sorbents to remove particles, moisture, and oil mist. In embodiments, various configurations of mist separators, air dryers, and particle filters may be used. In embodiments, the filters and sorbents include, in sequence, a mist separator, a micro mist separator, a membrane air dryer, a super mist separator, and an odor removal filter. An exemplary system of filters and sorbents for creating clean dry air includes, without limitation, an AFM30-N03-Z-A mist separator, an AFD30-N03-Z-A micro mist separator, an IDG10-N03 membrane air dryer, an AME250C-N03 super mist separator, and an AMF250C-N03 odor removal filter, all manufactured by the SMC Corporation.

In embodiments, the inlet gas supply, such as, for example clean dry air, is provided to the inlet 311 at a flow rate from greater than or equal to 5 L/min to less than or equal to 15 L/min, such as from greater than or equal to 7 L/min to less than or equal to 12 L/min. In some embodiments, the inlet gas supply is provided to the inlet 311 at a flow rate from greater than or equal to 8 L/min to less than or equal to 11 L/min, such as about 10 L/min. The flow rate of the inlet supply gas may be controlled using a regulator (not shown), such as, for example, an AR30-N03E-Z regulator manufactured by the SMC Corporation.

In embodiments, the oven 310 also comprises an outlet 312. The outlet 312 is, in embodiments, an orifice in the top of the oven 310. The outlet 312 allows hot gas to exit the oven 310 as exhaust gas. A volumetric portion of the exhaust gas is collected so that the VOCs present in the exhaust gas may be measured and analyzed. In embodiments, a manifold may be inserted into the outlet 312 to collect a volumetric portion of the exhaust gas. The size of the manifold is sufficient to collect a representative sample of the exhaust gas, but does not obstruct the flow of the exhaust gas through the outlet 312. In embodiments, the manifold may be a glass manifold or a stainless steel manifold.

The manifold that is present in the outlet 312 of the oven 310 is fluidly connected to the first trap 320. In embodiments, the first trap 320 comprises a sorbent that captures VOCs. In embodiments, the first trap is a thermal desorption tube, such as Carbotrap 300 manufactured by Sigma Aldrich, which contains graphitized carbon and carbon molecular sieves sorbents. It should be understood that other VOC-trapping sorbents may be used depending on the nature of the VOCs being collected. The exhaust gas that is captured by the manifold is, in embodiments, pulled through the first trap 320 at a flow rate from greater than or equal to 0.15 L/min to less than or equal to 0.35 L/min, such as from greater than or equal to 0.20 L/min to less than or equal to 0.30 L/min. In some embodiments, the gas that is captured by the manifold is pulled through the first trap 320 at a flow rate of about 0.25 L/min. In embodiments, the flow rate is determined by the desired sampling time, analytical instrument sensitivity, nature, and amount of VOCs.

In embodiments, downstream from the first trap 320 is a flow meter 330 that is fluidly connected to the first trap 320 and positioned to measure the flow rate of the exhaust gas through the first trap 320. The flow rate reading from the flow meter 330 is used to determine the gas flow rate through the first trap 320. The exhaust gas is pulled from the manifold in outlet 312 of the oven 310 by a pump 350 that is downstream from, and fluidly connected to, both the flow meter 330 and the first trap 320. Although the type of pump 350 is not particularly limited, in embodiments, the pump 350 may be a diaphragm pump, however any other suitable pump could be used, such as, for example bellows or vacuum pumps. In embodiments, the flow rate of the pump may be modified by a regulator 360 that controls the flow rate of the exhaust gas through the first trap 320. In some embodiments, the regulator 360 may be a rotameter with a needle valve, where the needle valve is used to modify the flow of exhaust gas through the VOC measurement system 300 by regulating the volume of exhaust gas that exits the VOC measurement system 300. In some embodiments, the gas flow rate through the VOC measurement system 300 is regulated by adjusting the pump.

In some embodiments, a second trap 340 is optionally positioned between the flow meter 330 and the pump 350. The second trap 340 may be the same as or different than the first trap 320 and prevents pulsation from the pump from effecting the flow rate of the exhaust gas through the flow meter 330. In this way a stable reading may be achieved on the flow meter 330.

Embodiments of methods for measuring VOCs using the apparatus described hereinabove and depicted in FIG. 3 are provided. In embodiments, one or more traps that may be used as the first trap 320 are conditioned and qualified before being used as the first trap 320 in the VOC measurement system 300. The conditioning comprises, according to embodiments, heating the one or more traps in a tube conditioner while running a purge gas across the traps. In embodiments, the traps are heated to a temperature from greater than or equal to 325° C. to less than or equal to 375° C., such as from greater than or equal to 335° C. to less than or equal to 365° C. In some embodiments, the traps are heated to a temperature from greater than or equal to 345° C. to less than or equal to 355° C., such as a temperature of about 350° C. The duration of the heating for the conditioning may be from greater than or equal to 9 hours to less than or equal to 15 hours, such as about 12 hours. In embodiments, the purge gas may be helium, nitrogen, argon, hydrogen, or mixtures thereof. The flow rate of the purge gas during the conditioning step may be from greater than or equal to 75 ml/min to less than or equal to 125 ml/min, such as from greater than or equal to 90 ml/min to less than or equal to 110 ml/min, in embodiments. In some embodiments, the flow rate of the purge gas in the conditioning step may be from greater than or equal to 95 ml/min to less than or equal to 105 ml/min, such as about 100 ml/min. After the traps are heated, they are allowed to cool while continuing the flow of the purge gas. An exemplary, non-limiting, conditioning apparatus is a TC-2 Tube conditioner manufactured by Gerstel.

The traps are cooled to room temperature after the conditioning step before they are qualified. In embodiments, the qualifying is conducted by loading one or more conditioned traps into a thermal desorption system (TDS) that is coupled to a gas chromatograph/mass spectrometer (GC-MS). The qualifying is conducted at the same temperature and for the same duration described below for VOC sampling. Each trap that shows no organics on GC-MS is considered qualified and stored for use as the first trap 320 in the VOC measurement system 300. An exemplary, non-limiting, TDS 3 is manufactured by Gerstel.

After the qualifying the traps, the oven 310 is turned on and the set-point temperature is set to the operating temperature (e.g., depyrogenation temperature) and the flow rate of the supply gas is adjusted to its operating flow rate. A qualified trap is inserted into the VOC measurement system 300 as the first trap 320, and the flow rate of the exhaust gas from the oven 310 and through the first trap 320 is adjusted to the operating flow rate. The oven exhaust gas is sampled with an empty oven 310 to obtain a background level of VOCs in the oven 310. The duration of the background sampling is, in embodiments, from greater than or equal to 45 minutes to less than or equal to 75 minutes, such as from greater than or equal to 55 minutes to less than or equal to 65 minutes. In embodiments, the duration of the background sampling is about 60 minutes. During the background sampling, the flow rate of the exhaust gas through the first trap 320 is monitored so that it remains at the operating flow rate. After the duration of the background sampling is complete, the first trap 320 is removed from the VOC measurement system 300 and loaded into the TDS where the VOC content is measure by GC-MS. The background amount of VOCs is then recorded for later comparison.

After the background VOCs are measured, a different qualified trap is inserted into the VOC measurement system 300 as the first trap 320. Coated glass containers are then loaded into the interior of the oven 310. Although the glass containers may be loaded into the oven in any way and in any configuration, in embodiments, the glass containers are placed onto one or more pyrolized Pyrex rack(s) having pins to accommodate the glass containers in an inverted position. The Pyrex rack may have at least 10 pins, such as at least 16 pins, or even at least 20 pins. Multiple Pyrex racks holding glass containers may then be loaded onto pyrolized stainless steel trays, and the stainless steel trays are loaded into the oven 310. In embodiments, at least 200 glass containers are loaded onto Pyrex rack(s) and inserted into the oven 310, such as at least 250 glass containers are loaded onto Pyrex rack(s) and inserted into the oven 310. Pyrex racks and trays are pyrolized, cleaned of the surface organics, by loading them into a hot oven at 300° C. or higher for 15 min or longer.

Once the oven 310 has been loaded with the coated glass containers, the oven 310 is heated to a temperature that is near the depyrogenation temperature, such as a temperature above 260° C., such as above 320° C., or even above 360° C. In embodiments, VOCs are collected on the first trap 320 for a duration from greater than or equal to 40 minutes to less than or equal to 80 minutes, such as from greater than or equal to 50 minutes to less than or equal to 70 minutes. In some embodiments, VOCs are collected on the first trap 320 for a duration from greater than or equal to 55 minutes to less than or equal to 65 minutes, such as about 60 minutes. During the collection of the VOCs, and according to embodiments, the pump 350 is operated and controlled by the regulator 360 to maintain a flow of exhaust gas across the first trap 320 at a rate from greater than or equal to 0.15 L/min to less than 0.35 L/min, such as from greater than or equal to 0.20 L/min to less than or equal to 0.30 L/min, or even about 0.25 L/min.

Once the VOCs have been collected in the first trap 320 for the desired duration, the pump 350 is turned off and the first trap 320 is removed. The trays holding the Pyrex racks and glass containers are removed from the oven 310. Subsequently, the first trap 320 that was used to capture VOCs is placed into a TDS coupled to a GC-MS and analyzed to determine the amount of VOCs released during the sampling.

To analyze the sample, the TDS containing the trap with the captured VOCs is heated from an initial temperature to a hold temperature at a heating rate of from greater than or equal to 50° C./min to less than or equal to 70° C./min, such as about 60° C./min. The initial temperature is, in embodiments, from greater than or equal to 35° C. to less than or equal to 45° C., such as about 40° C., and the hold temperature is greater than or equal to 340° C. to less than or equal to 360° C., such as about 350° C. The TDS is then held at the hold temperature for time period of greater than or equal to 5 minutes to less than or equal to 15 minutes, such as about 10 minutes. In some embodiments, during the analysis the traps were constantly purged with flowing helium, nitrogen, argon, hydrogen, and mixtures thereof at a flow rate of greater than or equal to 40 ml/min to less than or equal to 60 ml/min, such as about 50 ml/min. According to embodiments, the desorbing volatile and semi-volatile species are cryogenically focused, flash evaporated, and transferred into the GC column.

In embodiments, once the GC column is loaded with the sample, the GC column temperature is maintained at a temperature from greater than or equal to 35° C. to less than or equal to 45° C., such as about 40° C., for a time period of greater than or equal to 2 minutes to less than or equal to 7 minutes, such as about 5 minutes. Then the temperature of the GC column is increased to a hold temperature of greater than or equal to 310° C. to less than or equal to 330° C., such as about 320° C., at a heating rate of greater than or equal to 5° C./min to less than or equal to 15° C./min, such as about 10° C./min. The temperature of the GC column is held at the hold temperature for a time period of greater than or equal to 2 minutes to less than or equal to 7 minutes, such as about 5 minutes, to provide separation and purification of the volatile and semi-volatile organic species. The purified eluents from the GC column may, in embodiments, be analyzed by traditional electron impact ionization mass spectrometric protocols.

The peak area for each peak from the measured spectra is quantiated against a known standard to determine the amount of VOC species in the sample. Once the amount of VOCs from the sample is measured, the amount of VOCs is normalized to the split ratio of the oven exhaust. As described herein, the split ratio of the oven exhaust is the ratio of the total exhaust gas to the exhaust gas that is capture for the sample. In embodiments, the split ratio may be from greater than or equal to 20:1 to less than or equal to 60:1, such as from greater than or equal to 30:1 to less than or equal to 50:1. In some embodiments, the split ratio may be greater than or equal to 35:1 to less than or equal to 45:1, such as about 40:1. Accordingly, to normalize the VOCs to the split ratio, the measured amount of VOCs is modified according to the ratio. Subsequently, in embodiments, the amount of VOCs is normalized to 1 container by dividing the amount of VOCs normalized to the split ratio by the number of containers sampled.

Using the apparatuses and methods described herein, the VOCs evolved from coated glass containers can be accurately measured without breaking the glass containers, and multiple glass containers can be measured during one sampling. Further, the VOC measurements are more accurate at least because the evolution of VOCs is measured at conditions approximating actual heat treatment temperatures.

According to methods of embodiments, and with the use of apparatuses according to embodiments, the amount of VOCs emitted by a coated glass container may be measured. The methods and apparatuses of embodiments allows such measurements to be taken on multiple containers at a time without damaging the containers. Further, the VOC measurements obtained according to embodiments are more reliable at least because they are taken from intact containers at conditions that closely approximate depyrogenation conditions.

Although the methods and apparatuses for measuring VOCs of glass containers described above may be used with any coated glass container, in some embodiments, the coated glass container may be a glass container or package for containing pharmaceutical compositions, which will be described in detail below.

Conventional glass containers or glass packages for containing pharmaceutical compositions are generally formed from glass compositions that are known to exhibit chemical durability and low thermal expansion, such as Type IB alkali borosilicate glasses. While alkali borosilicate glasses exhibit good chemical durability, container manufacturers have observed silica-rich glass flakes dispersed in the solution contained in the glass containers. This phenomenon is referred to herein as delamination. Delamination occurs particularly when the solution has been stored in direct contact with the glass surface for long time periods (months to years). Accordingly, a glass which exhibits good chemical durability may not necessarily be resistant to delamination. Accordingly, glass compositions for glass packaging and processes for making glass packaging that reduce or eliminate delamination are disclosed in, for example, U.S. Patent Application Publication Nos. 2014/0151370 and 2013/0327740, which are incorporated herein by reference in their entirety.

Delamination refers to a phenomenon in which glass particles are released from the surface of the glass following a series of leaching, corrosion, and/or weathering reactions. In general, the glass particles are silica-rich flakes of glass which originate from the interior surface of the container as a result of the leaching of modifier ions into a solution contained within the container. These flakes may generally be from 1 nm to 2 μm thick with a width greater than about 50 μm. As these flakes are primarily composed of silica, the flakes generally do not further degrade after being released from the surface of the glass.

It has heretofore been hypothesized that delamination is due to phase separation that occurs in alkali borosilicate glasses when the glass is exposed to the elevated temperatures used for reforming the glass into a container shape. However, it is now believed that the delamination of the silica-rich glass flakes from the interior surfaces of the glass containers is due to the compositional characteristics of the glass container in its as-formed condition. Specifically, the high silica content of alkali borosilicate glasses causes the glass to have relatively high melting and forming temperatures. However, the alkali and borate components in the glass composition melt and/or vaporize at much lower temperatures. In particular, the borate species in the glass are highly volatile and evaporate from the surface of the glass at the high temperatures necessary to form and reform the glass.

Specifically, glass stock, such as a glass tube or the like, is reformed into glass containers at high temperatures and in direct flames. The high temperatures needed at higher equipment speeds cause the more volatile borate species to evaporate from portions of the surface of the glass. When this evaporation occurs within the interior volume of the glass container, the volatilized borate species are re-deposited in other areas of the glass container surface causing compositional heterogeneities in the glass container surface, particularly with respect to the near-surface regions of the interior of the glass container (i.e., those regions at or directly adjacent to the interior surfaces of the glass container).

Referring to FIG. 1 by way of example, a glass container, such as a glass container for storing a pharmaceutical composition, is schematically depicted in cross section. The glass container 100 generally comprises a glass article with a glass body 102. The glass body 102 extends between an interior surface 104 and an exterior surface 106 and generally encloses an interior volume 108. In the embodiment of the glass container 100 shown in FIG. 1, the glass body 102 generally comprises a wall portion 110 and a floor portion 112. The wall portions 110 and the floor portion 112 may generally have a thickness in a range from 0.5 mm to 3.0 mm. The wall portion 110 transitions into the floor portion 112 through a heel portion 114. The interior surface 104 and floor portion 112 are uncoated (i.e., they do not contain any inorganic coatings or organic coatings and, as such, the contents stored in the interior volume 108 of the glass container 100 are in direct contact with the glass from which the glass container 100 is formed. While the glass container 100 is depicted in FIG. 1 as having a specific shape form (i.e., a vial), it should be understood that the glass container 100 may have other shape forms, including, without limitation, vacutainers, cartridges, syringes, syringe barrels, ampoules, bottles, flasks, phials, tubes, beakers, or the like.

As noted herein, the glass container 100 may be formed by converting a glass tube into the container shape. For example, as one end of a glass tube is heated to close the glass tube and form the bottom or floor portion 112 of the container 100, more highly volatile species, such as borate species and/or alkali species or the like, may evaporate from the bottom portion of the tube and be re-deposited elsewhere in the tube. The evaporation of material from the heel and floor portions of the container is particularly pronounced as these areas of the container undergo the most extensive re-formation and, as such, are exposed to the highest temperatures. As a result, the areas of the container exposed to higher temperatures, such as the floor portion 112, may have silica-rich surfaces. Other areas of the interior surface 104 of the container which are amenable to deposition of the volatilized species, such as the wall portion 110, may have an interior surface layer 105 (schematically depicted in FIG. 2) formed by the condensation of the volatilized species and, as such, the surface is silica-poor. For example, in the case of borate species, areas amenable to boron deposition which are at a temperature greater than the anneal point of the glass composition but less than the hottest temperature the glass is subjected to during reformation can lead to boron incorporation on the surface of the glass.

Figure 2:
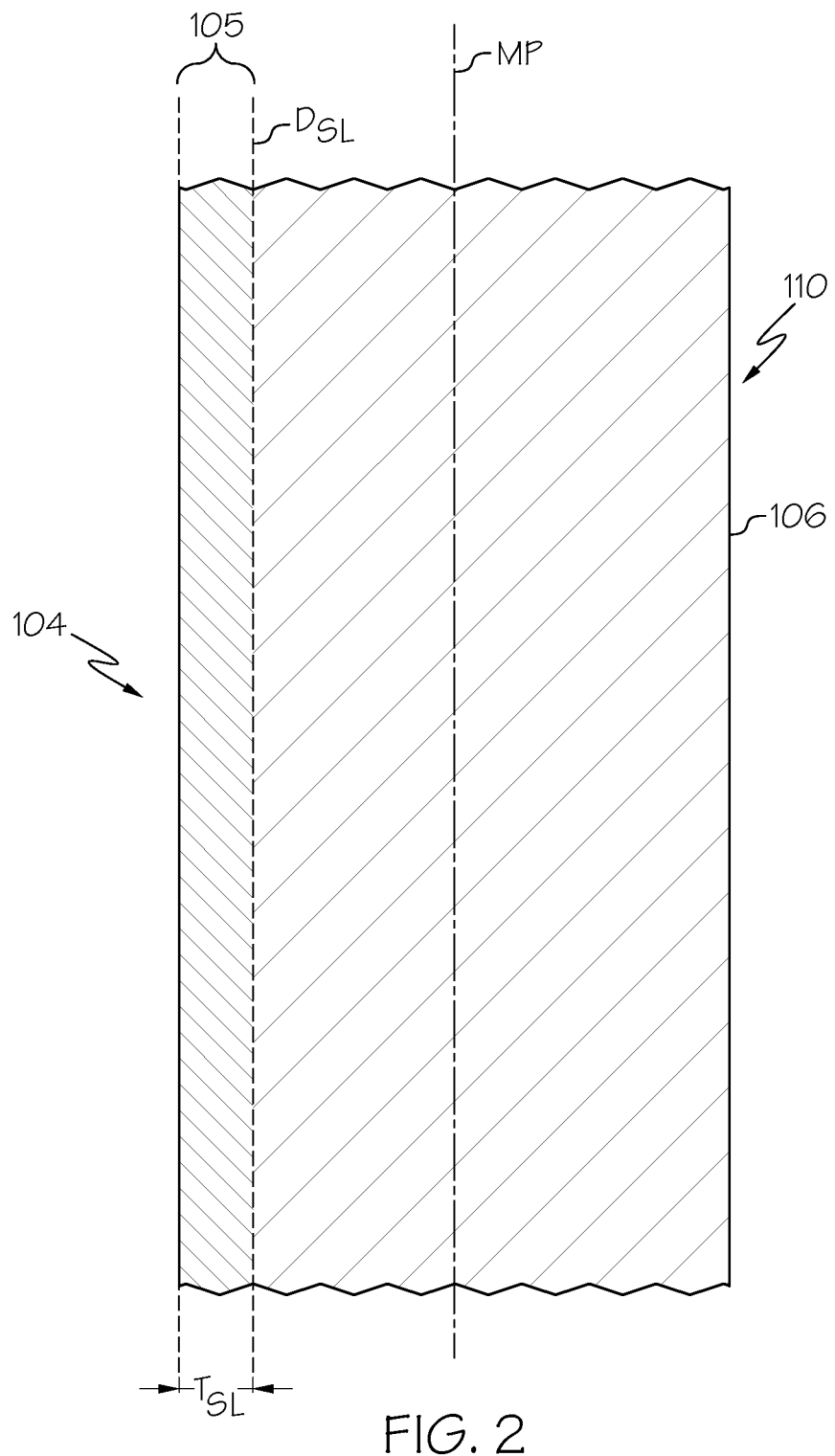
FIG. 2 schematically depicts a portion of the sidewall of the glass container of FIG. 1 prior to removal of the interior surface layer according to one or more embodiments described herein.

Referring now to FIGS. 1 and 2, the embodiment shown in FIG. 2 schematically depicts the interior surface 104 of a portion of a glass container 100, including the interior surface layer 105 which includes deposited volatilized species. The composition of the interior surface layer 105 is different than the composition of the glass deeper in the wall portion, such as at the midpoint MP of the wall portion 110. Specifically, FIG. 2 schematically depicts a partial cross section of a wall portion 110 of the glass container 100 of FIG. 1. The glass body 102 of the glass container 100 includes an interior surface layer 105 which extends from the interior surface 104 of the glass container 100 into the thickness of the wall portion 110 to a depth $D_{SL}$ from the interior surface 104 of the glass container. The glass composition within the interior surface layer 105 has a persistent layer heterogeneity relative to the glass at the midpoint MP of the wall portion and, as such, it should be understood that the composition of the glass in the interior surface layer 105 is different than the glass at the midpoint MP of the wall portion 110. In some embodiments, the thickness $T_{SL}$ of the interior surface layer is at least 30 nm. In some embodiments, the thickness $T_{SL}$ of the interior surface layer is at least 50 nm. In some embodiments, the thickness $T_{SL}$ of the interior surface layer is at least 100 nm. In some embodiments, the thickness $T_{SL}$ of the interior surface layer is at least 150 nm. In some other embodiments, the thickness $T_{SL}$ of the interior surface layer is at least 200 nm or even about 250 nm. In some other embodiments, the thickness $T_{SL}$ of the interior surface layer is at least 300 nm or even about 350 nm. In yet other embodiments, the thickness $T_{SL}$ of the interior surface layer is at least 500 nm. In some embodiments, the interior surface layer may extend to a thickness $T_{SL}$ of at least 1 µm or even at least 2 µm.

In the embodiments described herein, the phrase "persistent layer heterogeneity" means that the concentration of the constituent components (e.g., $SiO_2$, $Al_2O_3$, $Na_2O$, etc.) of the glass composition in the interior surface layer 105 vary from the concentration of the same constituent components at the midpoint of a thickness of the glass body (i.e., at a point along the midpoint line MP which evenly bisects the glass body between the interior surface 104 and the exterior surface 106) by an amount which would result in delamination of the glass body upon long term exposure to a solution contained within the glass container. In the embodiments described herein, the persistent layer heterogeneity in the interior surface layer of the glass body is such that an extrema (i.e., the minimum or maximum) of a layer concentration of each of the constituent components of the glass composition in the interior surface layer 105 is less than 92% or greater than 108% of the same constituent component at a midpoint of a thickness of the glass body when the glass container 100 is in as-formed condition. In other embodiments, the persistent layer heterogeneity in the interior surface layer 105 of the glass body is such that the extrema of the layer concentration of each of the constituent components of the glass composition in the interior surface layer 105 is less than 90% or greater than 110% of the same constituent component at the midpoint of the thickness of the glass body when the glass container 100 is in as-formed condition. In still other embodiments, the persistent layer heterogeneity in the interior surface layer 105 of the glass body is such that the extrema of the layer concentration of each of the constituent components of the glass composition in the interior surface layer 105 is less than 80% or greater than 120% of the same constituent component at the midpoint of the thickness of the glass body when the glass container 100 is in as-formed condition. In some embodiments, the persistent layer heterogeneity is exclusive of constituent components of the glass composition which are present in an amount less than 2 mol. %. The persistent layer heterogeneity is also exclusive of any water which may be present in the glass composition.

In the embodiments described herein, the phrase "persistent layer homogeneity" means that the concentration of the constituent components (e.g., $SiO_2$, $Al_2O_3$, $Na_2O$, etc.) of the glass composition in the interior region do not vary from the concentration of the same constituent components at the midpoint of a thickness of the glass body (i.e., at a point along the midpoint line MP which evenly bisects the glass body between the modified interior surface 104 and the exterior surface 106) by an amount which would result in delamination of the glass body upon long term exposure to a solution contained within the glass container. In the embodiments described herein, the persistent layer homogeneity in the interior region of the glass body is such that an extrema (i.e., the minimum or maximum) of a layer concentration of each of the constituent components of the glass composition in the interior region 120 is greater than or equal to 80% and less than or equal to 120% of the same constituent component at a midpoint of a thickness of the glass body after the interior surface layer with the persistent layer heterogeneity has been removed from the glass container. In other embodiments, the persistent layer homogeneity in the interior region of the glass body is such that the extrema of the layer concentration of each of the constituent components of the glass composition in the interior region 120 is greater than or equal to 90% and less than or equal to 110% of the same constituent component at the midpoint of the thickness of the glass body after the interior surface layer with the persistent layer heterogeneity has been removed from the glass container. In still other embodiments, the persistent layer homogeneity in the interior region of the glass body is such that the extrema of the layer concentration of each of the constituent components of the glass composition in the interior region 120 is greater than or equal to 92% and less than or equal to 108% of the same constituent component at the midpoint of the thickness of the glass body after the interior surface layer with the persistent layer heterogeneity has been removed from the glass container. In some embodiments, the persistent layer homogeneity is exclusive of constituent components of the glass composition which are present in an amount less than 2 mol. %. The persistent layer homogeneity is also exclusive of any water which may be present in the glass composition.

The term "as-formed condition," as used herein, refers to the composition of the glass container 100 after the glass container has been formed from glass stock but prior to the container being exposed to any additional processing steps, such as ion-exchange strengthening, coating, ammonium sulfate treatment, acid etching, and/or any other surface modifications. In the embodiments described herein, the layer concentration of the constituent components in the glass composition is determined by collecting a composition sample through the thickness of the glass body in the area of interest using dynamic secondary ion mass spectroscopy ("D-sims"). In the embodiments described herein, the composition profile is sampled from areas of the interior surface 104 of the glass body 102. The sampled areas have a maximum area of 1 mm$^2$. This technique yields a compositional profile of the species in the glass as a function of depth from the interior surface of the glass body for the sampled area.

When the glass container is formed from a borosilicate glass composition (such as a Type IB glass composition), the presence of the interior surface layer 105 containing deposited volatile species may also be ascertained qualitatively. Specifically, the glass container 100 may be filled with a solution of methylene blue dye. The methylene blue dye reacts with and chemically bonds to the boron-rich regions of the glass surface, visibly staining the areas blue. A suitable methylene blue dye solution may include, without limitation, a 1% solution of methylene blue in water.

If this interior surface layer 105 of deposited volatilized species remains on the interior surface 104, solutions contained in the container may leach the deposited volatilized species from the interior surface layer 105. As these volatilized species are leached from the glass, a high silica glass network (gel) remains on the interior surface 104 which swells and strains during hydration and eventually spalls from the surface (i.e., the interior surface 104 of the glass container 100 delaminates), potentially introducing particulate matter into the solution contained within the glass container.

One conventional solution to delamination is to coat the interior surface of the body of the glass container with an inorganic coating, such as $SiO_2$. This coating may have a thickness from 100 nm to 200 nm and prevents the contents of the container from contacting the interior surface of the body and causing delamination. However, the application of such coatings may be difficult and require additional manufacturing and/or inspection steps, thereby increasing the overall cost of container manufacture. Further, if the contents of the container penetrate the coating and contact the interior surface of the body, such as through a discontinuity in the coating, the resultant delamination of the glass body may cause portions of the coating to detach from the interior surface of the body.

In some embodiments, an interior surface layer 105 is removed from the wall portion 110 of the glass container by etching to reduce the propensity of the interior surface layer 105 to delaminate. For example, an aqueous treating medium may be introduced into the interior volume 108 and allowed to remain in the interior volume for a time sufficient to remove the thin interior surface layer 105. Suitable aqueous treating mediums will uniformly dissolve the thin interior surface layer 105. Specifically, the glass container 100 is generally formed from a glass composition which includes silica ($SiO_2$) as the primary network former and additional constituent components (e.g., $B_2O_3$, alkali oxides, alkaline earth oxides and the like) which are present in the silica network. However, the silica and the constituent components are not necessarily soluble in the same solutions or dissolve at the same rate in a solution. Accordingly, the aqueous treating medium may contain fluoride ions and/or one or more acids to facilitate a uniform dissolution of the glass network and additional constituent components contained in the interior surface layer 105. Suitable etchants are disclosed, for example, in U.S. patent application Ser. No. 14/949,320 filed on Nov. 23, 2015, which is incorporated herein in its entirety.

Removing a thin layer of the interior surface layer with the persistent layer heterogeneity or with persistent layer homogeneity, generally improves the resistance of the glass container to delamination. Specifically, removing volatilized species from the surface of the interior surface layer reduces the amount of these volatilized species that may be disassociated from the interior surface layer when the glass container is in use.

As noted above, delamination may result in the release of silica-rich glass flakes into a solution contained within the glass container after extended exposure to the solution. Accordingly, the resistance to delamination may be characterized by the number of glass particulates present in a solution contained within the glass container after exposure to the solution under specific conditions. In order to assess the long-term resistance of the glass container to delamination, an accelerated delamination test was utilized. The test was performed on both ion-exchanged and non-ion-exchanged glass containers. The test consisted of washing the glass container at room temperature for 1 minute and depyrogenating the container at about 320° C. for 1 hour. Thereafter a solution of 20 mM glycine with a pH of 10 in water is placed in the glass container to 80-90% fill, the glass container is closed, and rapidly heated to 100° C., and then heated from 100° C. to 121° C. at a ramp rate of 1 deg/min at a pressure of 2 atmospheres. The glass container and solution are held at this temperature for 60 minutes, cooled to room temperature at a rate of 0.5 deg/min and the heating cycle and hold are repeated. The glass container is then heated to 50° C. and held for ten or more days for elevated temperature conditioning. After heating, the glass container is dropped from a distance of at least 18" onto a firm surface, such as a laminated tile floor, to dislodge any flakes or particles that are weakly adhered to the inner surface of the glass container. The distance of the drop may be scaled appropriately to prevent larger sized vials from fracturing on impact.

Thereafter, the solution contained in the glass container is analyzed to determine the number of glass particles present per liter of solution. Specifically, the solution from the glass container is directly poured onto the center of a Millipore Isopore Membrane filter (Millipore # ATTP02500 held in an assembly with parts # AP1002500 and # M000025A0) attached to vacuum suction to draw the solution through the filter within 10-15 seconds for 5 mL. Thereafter, another 5 mL of water was used as rinse to remove buffer residue from the filter media. Particulate flakes are then counted by differential interference contrast microscopy (DIC) in the reflection mode as described in "Differential interference contrast (DIC) microscopy and modulation contrast microscopy" from Fundamentals of light microscopy and digital imaging. New York: Wiley-Liss, pp 153-168. The field of view is set to approximately 1.5 mm×1.5 mm and particles larger than 50 μm are counted manually. There are 9 such measurements made in the center of each filter membrane in a 3×3 pattern with no overlap between images. If larger areas of the filter media are analyzed, results can be normalized to equivalent area (i.e., 20.25 mm$^2$). The images collected from the optical microscope are examined with an image analysis program (Media Cybernetic's ImagePro Plus version 6.1) to measure and count the number of glass flakes present. This was accomplished as follows: all of the features within the image that appeared darker than the background by simple grayscale segmentation were highlighted; the length, width, area, and perimeter of all of the highlighted features that have a length greater than 25 micrometers are then measured; any obviously non-glass particles are then removed from the data; the measurement data is then exported into a spreadsheet. Then, all of the features greater than 25 micrometers in length and brighter than the background are extracted and measured; the length, width, area, perimeter, and X-Y aspect ratio of all of the highlighted features that have a length greater than 25 micrometers are measured; any obviously non-glass particles are removed from the data; and the measurement data is appended to the previously exported data in the spreadsheet. The data within the spreadsheet is then sorted by feature length and broken into bins according to size. The reported results are for features greater than 50 micrometers in length. Each of these groups was then counted and the counts reported for each of the samples.

A minimum of 100 mL of solution is tested. As such, the solution from a plurality of small containers may be pooled to bring the total amount of solution to 100 mL. For containers having a volume greater than 10 mL, the test is repeated for a trial of 10 containers formed from the same glass composition under the same processing conditions and the result of the particle count is averaged for the 10 containers to determine an average particle count. Alternatively, in the case of small containers, the test is repeated for a trial of 10 vials, each of which is analyzed and the particle count averaged over the multiple trials to determine an average particle count per trial. Averaging the particle count over multiple containers accounts for potential variations in the delamination behavior of individual containers. Table 1 summarizes some non-limiting examples of sample volumes and numbers of containers for testing:

TABLE 1

Exemplary Test Specimens

| Nominal Vial Capacity (mL) | Vial Max Volume (mL) | Minimum Solution per Vial (mL) | Number of Vials in a Trial | Number of Trials | Total Solution Tested (mL) |
|---|---|---|---|---|---|
| 2.0 | 4.0 | 3.2 | 10 | 4 | 128 |
| 3.5 | 7.0 | 5.6 | 10 | 2 | 112 |
| 4.0 | 6.0 | 4.8 | 10 | 3 | 144 |
| 5.0 | 10.0 | 8.0 | 10 | 2 | 160 |
| 6.0 | 10.0 | 8.0 | 10 | 2 | 160 |
| 8.0 | 11.5 | 9.2 | 10 | 2 | 184 |
| 10.0 | 13.5 | 10.8 | 10 | 1 | 108 |
| 20.0 | 26.0 | 20.8 | 10 | 1 | 208 |
| 30.0 | 37.5 | 30.0 | 10 | 1 | 300 |
| 50.0 | 63.0 | 50.4 | 10 | 1 | 504 |

It should be understood that the aforementioned test is used to identify particles which are shed from the interior wall(s) of the glass container due to delamination and not tramp particles present in the container from forming processes or particles which precipitate from the solution enclosed in the glass container as a result of reactions between the solution and the glass. Specifically, delamination particles may be differentiated from tramp glass particles based on the aspect ratio of the particle (i.e., the ratio of the maximum length of the particle to the thickness of the particle, or a ratio of the maximum and minimum dimensions). Delamination produces particulate flakes or lamellae which are irregularly shaped and typically have a maximum length greater than 50 μm but often greater than 200 μm. The thickness of the flakes is usually greater than 100 nm and may be as large as about 1 μm. Thus, the minimum aspect ratio of the flakes is typically greater than 50. The aspect ratio may be greater than 100 and sometimes greater than 1000. In contrast, tramp glass particles will generally have a low aspect ratio which is less than 3. Accordingly, particles resulting from delamination may be differentiated from tramp particles based on aspect ratio during observation with the microscope. Other common non-glass particles include hairs, fibers, metal particles, plastic particles, and other contaminants and are thus excluded during inspection. Validation of the results can be accomplished by evaluating interior regions of the tested containers. Upon observation, evidence of skin corrosion/pitting/flake removal, as described in "Nondestructive Detection of Glass Vial Inner Surface Morphology with Differential Interference Contrast Microscopy" from Journal of Pharmaceutical Sciences 101 (4), 2012, pages 1378-1384, is noted.

In the embodiments described herein, the number of particles present following accelerated delamination testing may be utilized to establish a delamination factor for the set of vials tested. In the embodiments described herein, trials of glass containers which average less than 10 glass particles with a minimum length of about 50 μm and an aspect ratio of greater than about 50 per trial following accelerated delamination testing are considered to have a delamination factor of 10. In the embodiments described herein, trials of glass containers which average less than 9 glass particles with a minimum length of about 50 μm and an aspect ratio of greater than 50 per trial following accelerated delamination testing are considered to have a delamination factor of 9. In the embodiments described herein, trials of glass containers which average less than 8 glass particles with a minimum length of about 50 µm and an aspect ratio of greater than 50 per trial following accelerated delamination testing are considered to have a delamination factor of 8. In the embodiments described herein, trials of glass containers which average less than 7 glass particles with a minimum length of about 50 µm and an aspect ratio of greater than 50 per trial following accelerated delamination testing are considered to have a delamination factor of 7. In the embodiments described herein, trials of glass containers which average less than 6 glass particles with a minimum length of about 50 µm and an aspect ratio of greater than 50 per trial following accelerated delamination testing are considered to have a delamination factor of 6. In the embodiments described herein, trials of glass containers which average less than 5 glass particles with a minimum length of about 50 µm and an aspect ratio of greater than 50 per trial following accelerated delamination testing are considered to have a delamination factor of 5. In the embodiments described herein, trials of glass containers which average less than 4 glass particles with a minimum length of about 50 µm and an aspect ratio of greater than 50 per trial following accelerated delamination testing are considered to have a delamination factor of 4. In the embodiments described herein, trials of glass containers which average less than 3 glass particles with a minimum length of about 50 µm and an aspect ratio of greater than 50 per trial following accelerated delamination testing are considered to have a delamination factor of 3. In the embodiments described herein, trials of glass containers which average less than 2 glass particles with a minimum length of about 50 µm and an aspect ratio of greater than 50 per trial following accelerated delamination testing are considered to have a delamination factor of 2. In the embodiments described herein, trials of glass containers which average less than 1 glass particle with a minimum length of about 50 µm and an aspect ratio of greater than 50 per trial following accelerated delamination testing are considered to have a delamination factor of 1. In the embodiments described herein, trials of glass containers which have 0 glass particles with a minimum length of about 50 µm and an aspect ratio of greater than 50 per trial following accelerated delamination testing are considered to have a delamination factor of 0. Accordingly, it should be understood that the lower the delamination factor, the better the resistance of the glass container to delamination. In the embodiments described herein, the glass containers have a delamination factor of 10 or lower (i.e., a delamination factor of 3, 2, 1 or 0) after the thin layer of the interior surface layer with the persistent layer heterogeneity has been removed from the glass container.

In the embodiments described herein, the glass containers may be formed from glass compositions which meet the criteria for Type I, Class A (Type IA) or Type I, Class B (Type IB) glasses under ASTM Standard E438-92 (2011) entitled "Standard Specification for Glasses in Laboratory Apparatus". Borosilicate glasses meet the Type I (A or B) criteria and are routinely used for pharmaceutical packaging. Examples of borosilicate glass include, without limitation, Corning® Pyrex® 7740, 7800, Wheaton 180, 200, and 400, Schott Duran®, Schott Fiolax®, KIMAX® N-51A, Gerresheimer GX-51 Flint and others.

The glass compositions from which the glass containers are formed are chemically durable and resistant to degradation, as determined by the ISO 720 standard. The ISO 720 standard is a measure of the resistance of the glass to degradation in distilled water (i.e., the hydrolytic resistance of the glass). In brief, the ISO 720 standard protocol utilizes crushed grass grains which are placed in contact with 18 MΩ water under autoclave conditions (121° C., 2 atm) for 30 minutes. The solution is then titrated colorimetrically with dilute HCl to neutral pH. The amount of HCl required to titrate to a neutral solution is then converted to an equivalent of $Na_2O$ extracted from the glass and reported in µg of glass with smaller values indicative of greater durability. The ISO 720 entitled "Testing of glass—Resistance to attack by a boiling aqueous solution of hydrochloric acid—Method of test and classification"; ISO 695:1991 entitled "Glass—Resistance to attack by a boiling aqueous solution of mixed alkali—Method of test and classification"; ISO 720:1985 entitled "Glass—Hydrolytic resistance of glass grains at 121 degrees C.—Method of test and classification"; and ISO 719:1985 "Glass—Hydrolytic resistance of glass grains at 98 degrees C.—Method of test and classification." Each standard and the classifications standard is broken into individual types. Type HGA1 is indicative of up to 62 µg extracted equivalent of $Na_2O$; Type HGA2 is indicative of more than 62 µg and up to 527 µg extracted equivalent of $Na_2O$; and Type HGA3 is indicative of more than 527 µg and up to 930 µg extracted equivalent of $Na_2O$. The glass containers described herein have an ISO 720 type HGA1 hydrolytic resistance after a thin layer of the interior surface layer with the persistent layer heterogeneity has been removed from the glass container.

The glass compositions from which the glass containers are formed are also chemically durable and resistant to degradation, as determined by the ISO 719 standard. The ISO 719 standard is a measure of the resistance of the glass to degradation in distilled water (i.e., the hydrolytic resistance of the glass). In brief, the ISO 719 standard protocol utilizes crushed glass grains which are placed in contact with 18 MΩ water at a pressure of 2 atm and a temperature of 98° C. for 60 minutes. The solution is then titrated colorimetrically with dilute HCl to neutral pH. The amount of HCl required to titrate to a neutral solution is then converted to an equivalent of $Na_2O$ extracted from the glass and reported in µg of glass with smaller values indicative of greater durability. The ISO 719 standard is broken into individual types. Type HGB1 is indicative of up to 31 µg extracted equivalent of $Na_2O$; Type HGB2 is indicative of more than 31 µg and up to 62 µg extracted equivalent of $Na_2O$; Type HGB3 is indicative of more than 62 µg and up to 264 µg extracted equivalent of $Na_2O$; Type HGB4 is indicative of more than 264 µg and up to 620 µg extracted equivalent of $Na_2O$; and Type HGB5 is indicative of more than 620 µg and up to 1085 µg extracted equivalent of $Na_2O$. The glass containers described herein have an ISO 719 type HGB1 hydrolytic resistance after the thin layer of the interior surface layer with the persistent layer heterogeneity has been removed from the glass container.

With respect to the USP <660> test and/or the European Pharmacopeia 3.2.1 test, the glass containers described herein have a Type 1 chemical durability after the thin layer of the interior surface layer with the persistent layer heterogeneity has been removed from the glass container. As noted above, the USP <660> and European Pharmacopeia 3.2.1 tests are performed on intact glass containers rather than crushed grains of glass and, as such, the USP <660> and European Pharmacopeia 3.2.1 tests may be used to directly assess the chemical durability of the interior surface of the glass containers.

The glass compositions from which the glass containers are formed are also chemically durable and resistant to degradation in acidic solutions, as determined by the DIN 12116 standard, after the thin layer of the interior surface layer with the persistent layer heterogeneity has been removed from the glass container. In brief, the DIN 12116 standard utilizes a polished glass sample of a known surface area which is weighed and then positioned in contact with a proportional amount of boiling 6 M hydrochloric acid for 6 hours. The sample is then removed from the solution, dried and weighed again. The glass mass lost during exposure to the acidic solution is a measure of the acid durability of the sample with smaller numbers indicative of greater durability. The results of the test are reported in units of half-mass per surface area, specifically mg/dm$^2$. The DIN 12116 standard is broken into individual classes. Class S1 indicates weight losses of up to 0.7 mg/dm$^2$; Class S2 indicates weight losses from 0.7 mg/dm$^2$ up to 1.5 mg/dm$^2$; Class S3 indicates weight losses from 1.5 mg/dm$^2$ up to 15 mg/dm$^2$; and Class S4 indicates weight losses of more than 15 mg/dm$^2$. The glass containers described herein have a DIN 12116 Class S2 acid resistance or better after the thin layer of the interior surface layer with the persistent layer heterogeneity has been removed from the glass container.

The glass compositions from which the glass containers are formed are also chemically durable and resistant to degradation in basic solutions, as determined by the ISO 695 standard, after the thin layer of the interior surface layer with the persistent layer heterogeneity has been removed from the glass container. In brief, the ISO 695 standard utilizes a polished glass sample which is weighed and then placed in a solution of boiling 1 M NaOH+0.5M Na$_2$CO$_3$ for 3 hours. The sample is then removed from the solution, dried and weighed again. The glass mass lost during exposure to the basic solution is a measure of the base durability of the sample with smaller numbers indicative of greater durability. As with the DIN 12116 standard, the results of the ISO 695 standard are reported in units of mass per surface area, specifically mg/dm$^2$. The ISO 695 standard is broken into individual classes. Class A1 indicates weight losses of up to 75 mg/dm$^2$; Class A2 indicates weight losses from 75 mg/dm$^2$ up to 175 mg/dm$^2$; and Class A3 indicates weight losses of more than 175 mg/dm$^2$. The glass containers described herein have an ISO 695 base resistance of Class A2 or better after the thin layer of the interior surface layer with the persistent layer heterogeneity has been removed from the glass container.

It should be understood that, when referring to the above referenced classifications according to ISO 695, ISO 719, ISO 720 or DIN 12116, a glass composition or glass container which has a specified classification "or better" means that the performance of the glass composition is as good as or better than the specified classification. For example, a glass container which has an ISO 695 base resistance of "Class A2" or better may have an ISO 695 classification of either Class A2 or Class A1.

Embodiments of the methods and apparatuses described herein will now be defined in various aspects. The following aspects are exemplary and do not limit other embodiments disclosed and described herein. It should be understood that any of the aspects described below may be combined with one or more other aspects In a first aspect a method for measuring volatile organic compounds evolved from one or more coated glass containers comprises: loading the one or more coated glass containers into an oven; heating the oven to a heat treatment temperature; purging the oven with dry clean air; collecting at least a volumetric portion of an oven exhaust; trapping volatile organic compounds from the volumetric portion of the oven exhaust in a trap; and measuring the volatile organic compounds trapped in the trap, wherein the one or more glass containers are in-tact.

A second aspect includes the method according to the first aspect, wherein the one or more glass containers comprise a low-friction coating.

A third aspect includes the method according to the first and second aspect, wherein the low-friction coating is thermally stable.

A fourth aspect includes the method according to the first through third aspects, wherein the low-friction coating comprises a coupling agent and a polymer.

A fifth aspect includes the method according to the fourth aspect, wherein the coupling agent is a silane and the polymer is a polyimide.

A sixth aspect includes the method according to the first through fifth aspects, wherein at least 200 in-tact glass containers are loaded into the oven.

A seventh aspect includes the method according to the first through sixth aspects, wherein the heat treatment temperature is a depyrogenation temperature.

An eighth aspect includes the method according to the first through seventh aspects, wherein the heat treatment temperature is above 260° C.

A ninth aspect includes the method according to the first through eighth aspects, wherein the heat treatment temperature is from greater than or equal to 320° C. to less than or equal to 335° C.

A tenth aspect includes the method according to the first through eighth aspects, wherein the heat treatment temperature is from greater than or equal to 360° C. to less than or equal to 375° C.

An eleventh aspect includes the method according to the first through tenth aspects, wherein a flow rate of the volumetric portion of the oven exhaust across the trap is from greater than or equal to 0.15 L/min to less than or equal to 0.35 L/min.

A twelfth aspect includes the method according to the first through tenth aspects, wherein a supply gas is provided to an inlet of the oven at a flow rate from greater than or equal to 5 L/min to less than or equal to 15 L/min.

A thirteenth aspect includes the method according to the first through twelfth aspects, wherein a split ratio of a total oven exhaust to the volumetric portion of the oven exhaust that is collected is from greater than or equal to 20:1 to less than or equal to 60:1.

A fourteenth aspect includes the method according to the first through thirteenth aspects, wherein the one or more glass containers have a delamination factor less than or equal to 10.

A fifteenth aspect includes the method according to the first through fourteenth aspects, wherein the one or more glass containers have a delamination factor less than or equal to 5.

A sixteenth aspect includes the method according to the first through fifteenth aspects, wherein the oven is purged with dry clean air for a time period that achieves a desirable residence time for VOCs in the oven.

A seventeenth aspect includes an apparatus for measuring an evolution of volatile organic compounds from a coated glass container comprising: an oven having an interior volume that is capable of holding one or more in-tact glass containers; a first trap fluidly connected to the oven; a flow meter fluidly connected to the first trap; and a pump fluidly connected to the flow meter, wherein a volumetric portion of an oven exhaust gas is directed to the first trap, the first trap collects volatile organic compounds from the volumetric portion of the oven exhaust gas, and the pump controls a flow rate of the volumetric portion of the oven exhaust gas across the first trap.

An eighteenth aspect includes the apparatus according to the seventeenth aspect, further comprising a second trap fluidly connected to the flow meter and the pump.

A nineteenth aspect includes the apparatus according to the seventeenth and eighteenth aspects, further comprising a regulator fluidly connected to the pump, wherein the regulator controls an amount of gas that exits the apparatus.

A twentieth aspect includes the apparatus according to the seventeenth through nineteenth aspects, wherein a flow rate of the volumetric portion of the oven exhaust across the first trap is from greater than or equal to 0.15 L/min to less than or equal to 0.35 L/min.

A twenty-first aspect includes the apparatus according to the seventeenth through twentieth aspects, wherein the interior volume of the oven is capable of holding at least 200 in-tact glass containers.

A twenty-second aspect includes the apparatus according to the seventeenth through twenty-first aspects, wherein the oven is purged with clean dry air to achieve a desirable residence time for VOCs in the oven.

EXAMPLE

Embodiments will be further clarified by the following example for measuring VOCs of glass containers.

Initially, a Carbotrap 300 was conditioned using a Gerstel TC-2 Tube conditioner. Twelve traps were loaded into the tube conditioner. The traps were then conditioned at 350° C. for 12 hours using a 100 ml/min helium gas purge across the traps. The traps were then cooled to room temperature in the tube conditioner while maintaining the flow of helium gas.

After conditioning, the traps were qualified with a Gerstel TDS coupled to a GC-MS. The TDS was heated from 40° C. to 350° C. at a heating rate of 60° C./min and held for 10 minutes at this temperature. The traps were constantly purged with flowing helium at a flow rate of 50 mL/min. The desorbing volatile and semi-volatile species were cryogenically focused and were then flash evaporated and transferred into the GC column. The GC column temperature was maintained at 40° C. for 5 minutes, and then increased to 320° C. at a rate of 10° C./min and held at 320° C. for 5 minutes to provide a separation and purification of the volatile and semi-volatile organic species. The traps were qualified if they show a clean, flat baseline void of VOCs.

A qualified trap was then loaded into the VOC measurement system. The VOC background in the oven was then measured by heating the oven to 320° C. A flow of clean dry air was set to 10 L/min, and the flow rate through the trap was set to 0.25 L/min. The exhaust of the oven was sampled for 60 minutes while periodically adjusting the flow rate through the trap to maintain the flow rate at 0.25 L/min. The thermal desorption from the trap was performed using a Gerstel TDS coupled to GC-MS system.

After collecting a background sample, the trap used for the background sample was replaced with another prequalified trap. The oven was loaded with 200 coated glass containers were placed in an inverted orientation on 10 Pyrex racks—each having 20 pins. The Pyrex racks holding the glass containers were then placed on stainless steel trays and loaded into the oven. The oven was run at 320° C., and the exhaust gas from the oven was collected for 60 minutes with a flow rate of 0.25 L/min through the trap.

After the 60 minute collection time, the pump was turned off and the trap was disconnected and transferred to a Gerstel TDS. The glass containers were removed from the oven and allowed to cool at ambient temperature. The oven was then baked out overnight at 400° C. with the trays and racks loaded into the oven.

The TDS with the trap from the collection was heated from 40° C. to 350° C. at a heating rate of 60° C./min and held for 10 minutes at this temperature. The traps were constantly purged with flowing helium at 50 mL/min. The desorbing volatile and semi-volatile species were cryogenically focused, flash evaporated, and transferred into the GC column. The GC column temperature was maintained at 40° C. for 5 minutes, and then increased to 320° C. at a rate of 10° C./min. The GC column was then held at 320° C. for 5 minutes to provide a separation and purification of the volatile and semi-volatile organic species. This resulted in a distillation chromatogram, as the mechanism of separation of different organic species was based on the heat of vaporization. The purified eluents from the GC column were analyzed by traditional electron impact ionization mass spectrometric protocols. By operating under standardized conditions, the resulting mass spectra can be compared to existing mass spectral library databases for the purpose of spectral matching or component identification. The mass spectrum was scanned using a mass range from 41 to 550 atomic mass units.

The peak area for each peak from the measured spectra was quantiated against a known standard. Three calibration compounds were used: hexadecane, dicamethylcyclopentacylosiloxane, and benzaldehyde were used to represent alkanes/aliphatics, siloxanes, and aromatics. The calibration amount was 100 ng each and 4 replicates were averaged for each calibration compound.

Using an extracted ion mode input mass 53 a.m.u. and set the mass range to plus 1 a.m.u. and minus 3 a.m.u. to include masses 50-54, the total ion chromatogram was integrated from 0.0 to 5.0 minutes to extract only the selected masses from coeluting $CO_2$, 2-propenenitrile peak. The resulting peak for the extracted masses was integrated using integration events method "PN oven.e" to get the total area under the peak.

A standard concentration for 2-propenenitrile (400 ng) was spiked on a Carbotrap 300 and run using the same conditions as defined above for the sample. The resulting peak area for the 400 ng standard was then used as the response factor. The 2-propenenitrile concentration of the sample was calculated by dividing the sample peak area by the standard peak area response factor and multiplying by 400 (the standard concentration of 400 ng), multiplying by 40 (the oven split ratio of 40:1) and dividing by 200 (the number of containers) to normalize to a single container. Results of the calibration are shown in Table 2.

TABLE 2

| Compound | Benzaldehyde, 100 ng | Decamethylpentacyclosiloxane, 100 ng | Hexadecane, 100 ng | 2-propenenitrile, 400 ng |
|---|---|---|---|---|
| Injection 1 | 85800359 | 13797603 | 62394193 | 18475927 |
| Injection 2 | 1.13E+08 | 23208912 | 90990461 | 13532503 |
| Injection 3 | 55004320 | 19923356 | 58174579 | 13412026 |
| Injection 4 | 1.46E+08 | 14545078 | 89704353 | 2290733 |
| Average | 99750420 | 17868737 | 75315897 | 16927797 |

The Macro embedded within an Agilent Chemstation and NiST Automated Mass Spectral Deconvolution and Identification Software (AMDIS) was performed using two standardized integrations for each chromatogram. After a retention time of 2.6 minutes, the total ion chromatogram was integrated by the integration parameters, with the following set points:

| | |
|---|---|
| Initial Area Reject | 1 |
| Initial Peak Width | 0.2 |
| Shoulder Detection | off |
| Initial Threshold | 16 |
| Integrator Off | 0 |
| Integrator On | 2.6 |

The retention time from 0 to 2.6 minutes was integrated using the same parameters, except that the chromatogram was in the extracted ion chromatogram mode set to m/z of 53 Da, which was the base peak and molecular ion for 2-propenenitrile. A 400 ng/microliter standard of 2-propenenitrile was analyzed and the extracted ion chromatogram mode of operation was used to quantify the amounts. This determined the total area counts as well as individual area counts of the chromatographic peaks exceeding the above detection criteria for quantification. Subsequently, the top 30 or less abundant peaks meeting a probability based best match of 85% or 850 in AMDIS were identified and reported. Those failing to meet these criteria were reported as unknown.

As is usual when using such macros, the macro was manually checked to determine whether it adequately reflected the total peak area under the peaks. Namely, poor baseline interpolation can lead to skewed results. An example of a poor fitting baseline is shown in FIG. 4.

Figure 4:
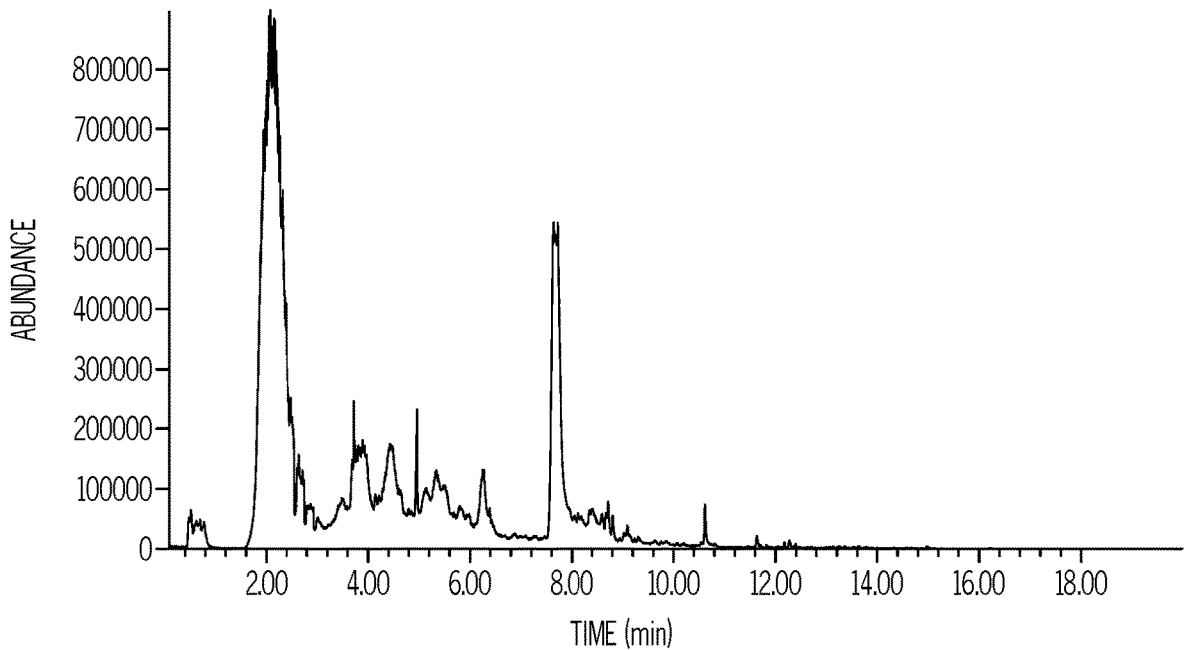
FIG. 4 is a GC-MS mass spectrum of VOCs according to one or more embodiments described herein.
Figure 5:
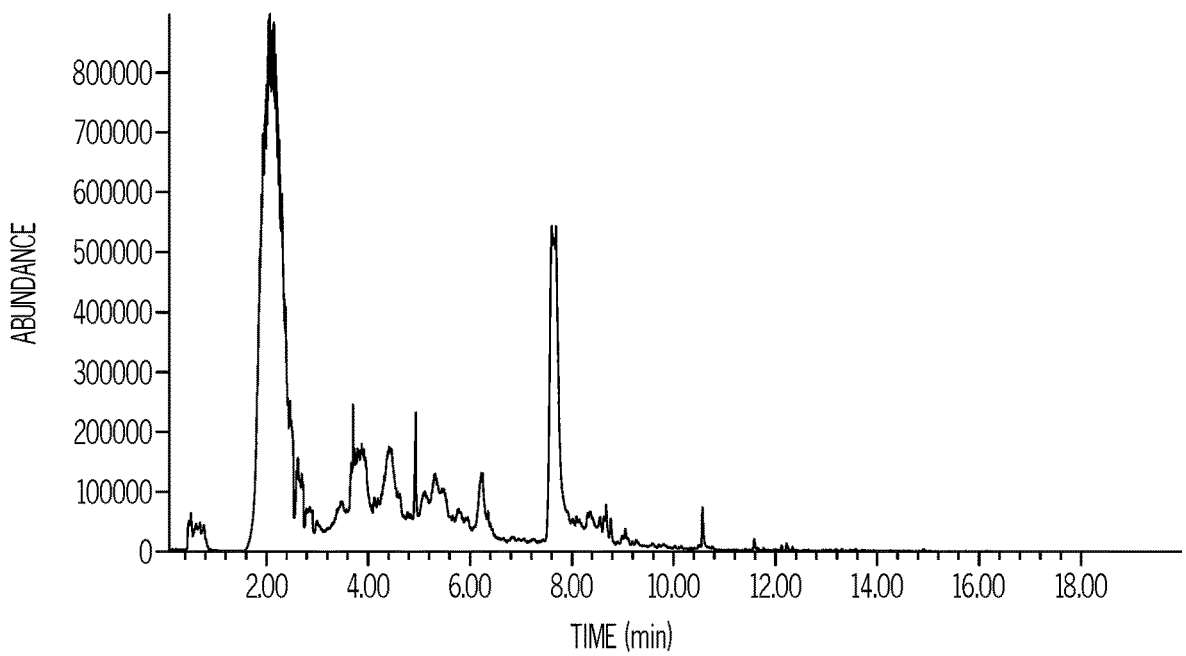
FIG. 5 is a GC-MS mass spectrum of VOCs according to one or more embodiments described herein.

In FIG. 4, the threshold at 16 shows horizontal lines having a peak to valley baseline, which incorporates additional peaks not related to the VOCs. This reflects an inaccurate peak for the VOCs. To make a more representative baseline fit, either the initial threshold can be adjusted, or the entire chromatogram may be manually fit. An example of an adjustment to the threshold is shown in FIG. 5, where the threshold was adjusted from 16 (as was shown in FIG. 4) to 17.

When the threshold was adjusted to 17, a valley to valley baseline reflects accurate peak areas for VOCs. By adjusting the macro to the appropriate threshold, the reported VOCs for this spectrum decreases from 68 to 46 ng/container.

The process outlined above was run for two samples (each sample testing 200 containers). The total VOCs for Sample 1 was 267 ng/container, and the total VOCs for Sample 2 was 278 ng/container. The background of the oven was also measured twice; once before the Samples 1 and 2 were tested and once after Samples 1 and 2 were tested. The pre-sample background measurement showed total VOCs of 26 ng/container and the post-sample measurement showed a total VOCs of 46 ng/container. The speciation of the VOCs in the background samples show that they were high in cyclic siloxane species that were not a VOC from the coating or the container, but an artifact of the measurement. Accordingly, these values were accounted for in the VOC calculations. Detailed results of measurements are shown in the tables below:

TABLE 3

Pre-Sample Oven Background

| Species | Time (min) | Area | Measured VOCs (ng) | VOCs Normalized to split ratio | VOCs Normalized to 1 container |
|---|---|---|---|---|---|
| Unknown (mass 60) | 3.71 | 19716567 | 26.18 | 1047.14 | 5.24 |
| Unknown (mass 60) | 4.112 | 2883090 | 3.83 | 153.12 | 0.77 |
| Aromatic | 5.35 | 6565917 | 6.58 | 263.29 | 1.32 |
| Unknown (mass 57) | 5.934 | 4268921 | 5.67 | 226.72 | 1.13 |
| Ketone functionality | 6.067 | 1131113 | 1.50 | 60.07 | 0.30 |
| Octanal | 8.685 | 2230006 | 2.96 | 118.43 | 0.59 |
| Cyclotetrasiloxane, octamethyl | 8.806 | 1224745 | 6.85 | 274.16 | 1.37 |
| Aromatic | 9.029 | 5217959 | 5.23 | 209.24 | 1.05 |
| 1-Hexanol, 2 ethyl | 9.304 | 3320199 | 4.41 | 176.33 | 0.88 |
| Nonanal | 10.614 | 1587047 | 2.11 | 84.29 | 0.42 |
| Cyclotetrasiloxane, decamethyl | 11.626 | 2595174 | 14.52 | 580.94 | 2.90 |
| Aliphatic | 13.734 | 879025 | 1.17 | 46.68 | 0.23 |
| Alkane 14.969 | 14.969 | 1039152 | 1.38 | 55.19 | 0.28 |
| Total | | | 129.50 | | 25.90 |

TABLE 4

| | | Sample 1 | | | |
|---|---|---|---|---|---|
| Species | Time (min) | Area | Measured VOCs (ng) | VOCs Normalized to split ratio | VOCs Normalized to 1 container |
| Propenenitrile | | | | | 198.94 |
| Unknown alphatic | 3.459 | 10092130 | 13.40 | 535.99 | 2.68 |
| Unknown alphatic | 3.804 | 5274800 | 7.00 | 280.14 | 1.40 |
| Unknown alphatic | 3.927 | 7844488 | 10.42 | 416.62 | 2.08 |
| Unknown (mass 60) | 4.263 | 85201799 | 113.13 | 4525.04 | 22.63 |
| Unknown alphatic | 5.36 | 48798533 | 64.79 | 2591.67 | 12.96 |
| Acetic acid | 5.706 | 29558791 | 39.25 | 1569.86 | 7.85 |
| Alkane | 6.251 | 15972061 | 21.21 | 848.27 | 4.24 |
| Benzaldehyde | 7.633 | 28846576 | 28.92 | 1156.75 | 5.78 |
| Aromatic | 8.41 | 2769535 | 2.78 | 111.06 | 0.56 |
| Octanal | 8.806 | 1373034 | 1.82 | 72.92 | 0.36 |
| Unknown | 9.094 | 3844053 | | | |
| 1-Hexanol, 2-ethyl | 9.295 | 4272089 | 5.67 | 226.89 | 1.13 |
| Acetophenone | 9.863 | 4421071 | 4.43 | 177.29 | 0.89 |
| Aromatic | 10.192 | 2133468 | 2.14 | 85.55 | 0.43 |
| Nonanal | 10.607 | 3771427 | 5.01 | 200.30 | 1.00 |
| Aromatic (mass 128) | 11.805 | 2040449 | 2.05 | 81.82 | 0.41 |
| Cyclopentasiloxane, decamethyl | 11.62 | 2791623 | | | |
| Aromatic (mass 128) | 11.805 | 1482153 | 1.49 | 59.43 | 0.30 |
| Decanal | 12.255 | 2111248 | 2.80 | 112.13 | 0.56 |
| Undecanal | 13.723 | 773314 | 1.03 | 41.07 | 0.21 |
| Dodecanoic acid, methyl | 16.503 | 11488927 | 15.25 | 610.17 | 3.05 |
| Total | | | | | 267.45 |

TABLE 5

| | | Sample 2 | | | |
|---|---|---|---|---|---|
| Species | Time (min) | Area | Measured VOCs (ng) | VOCs Normalized to split ratio | VOCs Normalized to 1 container |
| Propenenitrile | | | | | 209.03 |
| Unknown (mass 60) | 3.792 | 31630374 | 42.00 | 1679.88 | 8.40 |
| Cyclotrisiloxane, hexamethyl | 4.437 | 31982355 | 178.98 | 7159.40 | 35.80 |
| Acetic acid | 4.882 | 13584180 | 18.04 | 721.45 | 3.61 |
| Unknown aliphatic | 5.333 | 10442811 | 13.87 | 554.61 | 2.77 |
| Pyridine, 3 methyl | 5.506 | 13260809 | 17.61 | 704.28 | 3.52 |
| Alkane | 6.247 | 12502363 | 16.60 | 664.00 | 3.32 |
| Benzaldehyde | 7.631 | 32992594 | 33.08 | 1323.01 | 6.62 |
| Cyclotetrasiloxane, octamethyl | 8.809 | 810394 | 4.54 | 181.41 | 0.91 |
| Nonanal | 10.609 | 2924915 | 3.88 | 155.34 | 0.78 |
| Cyclopentasiloxane, decamethyl | 11.622 | 1415293 | | | |
| Decanal | 12.256 | 1825228 | 2.42 | 96.94 | 0.48 |
| Undecanal | 13.724 | 1324869 | 1.76 | 70.36 | 0.35 |
| Dodecanoic acid, methyl ester | 16.502 | 8366986 | 11.11 | 444.37 | 2.22 |
| Total | | | | | 277.80 |

TABLE 5

| | | Post-Sample Oven Background | | | |
|---|---|---|---|---|---|
| Species | Time (min) | Area | Measured VOCs (ng) | VOCs Normalized to split ratio | VOCs Normalized to 1 container |
| Unknown (mass 60) | 3.728 | 10611207 | 14.09 | 563.56 | 2.82 |
| Unknown aliphatic | 3.897 | 9472757 | 12.58 | 503.09 | 2.52 |
| Cyclotrisiloxane, hexamethyl | 4.444 | 18543084 | 103.77 | 4150.96 | 20.75 |

TABLE 5-continued

Post-Sample Oven Background

| Species | Time (min) | Area | Measured VOCs (ng) | VOCs Normalized to split ratio | VOCs Normalized to 1 container |
|---|---|---|---|---|---|
| Acetic acid | 4.952 | 2913716 | 3.87 | 154.75 | 0.77 |
| Unknown alphatic | 5.335 | 11212814 | 14.89 | 595.51 | 2.98 |
| Alkane | 6.253 | 9385767 | 12.46 | 498.47 | 2.49 |
| Benzaldehyde | 7.687 | 63176740 | 63.33 | 2533.39 | 12.67 |
| Nonanal | 10.617 | 2251147 | 2.99 | 119.56 | 0.60 |
| Total | | | 227.98 | | 45.60 |

In the above tables, time is represented on the x-axis of the spectra (such as the spectra shown in FIG. 5) where the peak for that species was located, area was the area under the peak measure by ionic current the measured VOCs was the amount of the VOCs captured in the Carbotrap 300 in nanograms; the VOCs normalized to the split ratio was the amount of VOCs captured in the Carbotrap 300 multiplied by ratio of oven exhaust captured to oven exhaust that was not captured; and the VOCs normalized to one container was the VOCs normalized to split ratio divided by the number of containers sampled. Accordingly, in this example, the VOCs normalized to the split ratio was the measured VOCs multiplied by 40 (the ratio of oven exhaust capture to oven exhaust not captured was 40:1), and the VOCs normalized to 1 container was the VOCs normalized to the split ratio divided by 200 containers sampled.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

The invention claimed is:

1. A method for measuring volatile organic compounds evolved from one or more coated glass containers, the method comprising:
loading at least 200 coated glass containers into an oven;
heating the oven to a heat treatment temperature;
purging the oven with dry clean air;
collecting at least a volumetric portion of an oven exhaust;
trapping volatile organic compounds from the volumetric portion of the oven exhaust in a trap;
measuring the volatile organic compounds trapped in the trap; and
normalizing the volatile organic compounds to a single container.

2. The method according to claim 1, wherein the glass containers comprise a low-friction coating.

3. The method according to claim 2, wherein the low-friction coating is thermally stable.

4. The method according to claim 2, wherein the low-friction coating comprises a coupling agent and a polymer.

5. The method according to claim 4, wherein the coupling agent is a silane and the polymer is a polyimide.

6. The method according to claim 1, wherein the at least 200 glass containers are loaded into the oven as in-tact glass containers.

7. The method according to claim 1, wherein the heat treatment temperature is a depyrogenation temperature.

8. The method according to claim 1, wherein the heat treatment temperature is above 260° C.

9. The method according to claim 1, wherein the heat treatment temperature is from greater than or equal to 320° C. to less than or equal to 335° C.

10. The method according to claim 1, wherein the heat treatment temperature is from greater than or equal to 360° C. to less than or equal to 375° C.

11. The method according to claim 1, wherein a flow rate of the volumetric portion of the oven exhaust across the trap is from greater than or equal to 0.15 L/min to less than or equal to 0.35 L/min.

12. The method according to claim 1, wherein a supply gas is provided to an inlet of the oven at a flow rate from greater than or equal to 5 L/min to less than or equal to 15 L/min.

13. The method according to claim 1, wherein a split ratio of a total oven exhaust to the volumetric portion of the oven exhaust that is collected is from greater than or equal to 20:1 to less than or equal to 60:1.

14. The method according to claim 1, wherein the glass containers have a delamination factor less than or equal to 10.

15. The method according to claim 14, wherein the glass containers have a delamination factor less than or equal to 5.

16. The method according to claim 1, wherein the oven is purged with dry clean air for a time period that achieves a desirable residence time for VOCs in the oven.

17. A method for measuring volatile organic compounds evolved from one or more coated glass containers, the method comprising:
loading at least 200 coated glass containers into an oven;
heating the oven to a heat treatment temperature;
purging the oven with dry clean air;
collecting at least a volumetric portion of an oven exhaust;
trapping volatile organic compounds from the volumetric portion of the oven exhaust in a trap; and
measuring the volatile organic compounds trapped in the trap, wherein
a flow rate of the volumetric portion of the oven exhaust across the trap is from greater than or equal to 0.15 L/min to less than or equal to 0.35 L/min.

18. The method according to claim 17, wherein a supply gas is provided to an inlet of the oven at a flow rate from greater than or equal to 5 L/min to less than or equal to 15 L/min.

19. The method according to claim 17, wherein a split ratio of a total oven exhaust to the volumetric portion of the oven exhaust that is collected is from greater than or equal to 20:1 to less than or equal to 60:1.

* * * * *